United States Patent
Perelman

(10) Patent No.: US 11,931,163 B2
(45) Date of Patent: Mar. 19, 2024

(54) METHOD AND APPARATUS TO DETERMINE THE MALIGNANT POTENTIAL OF PANCREATIC CYSTS USING LIGHT SCATTERING SPECTROSCOPY

(71) Applicant: Beth Israel Deaconess Medical Center, Inc., Boston, MA (US)

(72) Inventor: Lev T. Perelman, Brookline, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 967 days.

(21) Appl. No.: 16/487,768

(22) PCT Filed: Feb. 23, 2018

(86) PCT No.: PCT/US2018/019563
§ 371 (c)(1),
(2) Date: Aug. 21, 2019

(87) PCT Pub. No.: WO2018/156984
PCT Pub. Date: Aug. 30, 2018

(65) Prior Publication Data
US 2020/0297266 A1 Sep. 24, 2020

Related U.S. Application Data

(60) Provisional application No. 62/469,982, filed on Mar. 10, 2017, provisional application No. 62/462,510, filed on Feb. 23, 2017.

(51) Int. Cl.
*A61B 5/00* (2006.01)
*A61B 8/08* (2006.01)
*A61B 10/00* (2006.01)

(52) U.S. Cl.
CPC ............ *A61B 5/425* (2013.01); *A61B 5/0075* (2013.01); *A61B 5/0084* (2013.01);
(Continued)

(58) Field of Classification Search
CPC ..... A61B 5/425; A61B 5/0075; A61B 5/0084; A61B 8/0841; A61B 10/0045;
(Continued)

(56) References Cited

U.S. PATENT DOCUMENTS

| 4,566,438 A | 1/1986 | Liese et al. |
| 2003/0076493 A1 * | 4/2003 | Olsson ............ H04B 10/07955 356/327 |

(Continued)

FOREIGN PATENT DOCUMENTS

| WO | WO 2004/016155 A2 | 2/2004 |
| WO | WO-2016149701 A1 * | 9/2016 ........... A61B 5/0084 |

OTHER PUBLICATIONS

PCT/US2018/019563, Apr. 4, 2018, Invitation to Pay Additional Fees.
(Continued)

*Primary Examiner* — Baisakhi Roy
*Assistant Examiner* — Kaitlyn E Sebastian
(74) *Attorney, Agent, or Firm* — Wolf, Greenfield & Sacks, P.C.

(57) ABSTRACT

Described herein are embodiments of an approach to diagnosing pancreatic cystic lesions using light scattering spectroscopy. In some embodiments, the approach includes an apparatus including a spatial gating probe to isolate light reflected by the epithelial tissue of the internal cyst surface using spatial gating. In some further embodiments, the apparatus includes a scanning fiber probe that is capable of rotational and linear motion in order to scan the entire internal surface of the cyst. Use of such an approach may be (Continued)

advantageous to improve the accuracy of diagnosing pancreatic cystic lesions as cancerous, precancerous, or benign.

17 Claims, 15 Drawing Sheets

(52) U.S. Cl.
CPC ........ *A61B 8/0841* (2013.01); *A61B 10/0045* (2013.01); *A61B 2010/0061* (2013.01); *A61B 2562/0242* (2013.01)

(58) Field of Classification Search
CPC .... A61B 2010/0061; A61B 2562/0242; A61B 5/055; A61B 2562/0233; A61B 5/0062; A61B 5/7264; G16H 50/20
See application file for complete search history.

(56) References Cited

U.S. PATENT DOCUMENTS

| | | | | |
|---|---|---|---|---|
| 2007/0203404 A1* | 8/2007 | Zysk | ................... | A61B 5/6848 600/310 |
| 2009/0009759 A1* | 1/2009 | Backman | .............. | G01J 3/0208 356/303 |
| 2009/0204009 A1* | 8/2009 | Powers | ................ | A61B 5/1455 600/476 |
| 2009/0317856 A1* | 12/2009 | Mycek | ............... | G01N 21/6408 435/29 |
| 2012/0041290 A1* | 2/2012 | Perelman | ............. | A61B 5/0071 600/326 |
| 2014/0046163 A1 | 2/2014 | Swoyer et al. | | |

OTHER PUBLICATIONS

PCT/2018/019563, Jun. 11, 2018, International Search Report and Written Opinion.
PCT/US2018/019563, Sep. 6, 2019, International Preliminary Report on Patentability.
Invitation to Pay Additional Fees dated Apr. 4, 2018 in connection with International Application No. PCT/US2018/019563.
International Search Report and Written Opinion dated Jun. 11, 2018 in connection with International Application No. PCT/US2018/019563.
International Preliminary Report on Patentability dated Sep. 6, 2019 in connection with International Application No. PCT/US2018/019563.
Zhang et al., Light scattering spectroscopy identifies the malignant potential of pancreatic cysts during endoscopy. Nat Biomed Eng 1, 0040 (Mar. 13, 2017) doi:10.1038/s41551-017-0040.
Perelman et al., Observation of Periodic Fine Structure in Reflectance from Biological Tissue: A New Technique for Measuring Nuclear Size Distribution. Physical Review Letters; Jan. 19, 1998. vol. 80(3); pp. 627-630.

* cited by examiner

800

| Cyst | MRI/CT | CEA (ng/ml) | Cytology | Histopathology cyst type | Histopathology diagnosis | LSS Δ | LSS diagnosis |
|---|---|---|---|---|---|---|---|
| 1[a] | CNET | 686 | - | IPMN | LGD | 0.11 | LGD |
| 2[a] | - | - | - | Serous | Benign | 0.07 | Benign |
| 3 | Serous | 67 | Scant benign cells | IPMN | LGD | 0.12 | LGD |
| 4 | IPMN | 142 | - | IPMN | HGD | 0.74 | HGD |
| 5 | IPMN | 430 | LGD IPMN | IPMN | LGD | 0.19 | LGD |
| 6 | - | - | - | Pseudocyst | Benign | 0.08 | Benign |
| 7 | - | - | HGD IPMN | IPMN | HGD | 0.76 | HGD |
| 8 | IPMN | 1.8 | HGD IPMN | IPMN | HGD | 0.19 | LGD |
| 9 | IPMN | 151 | HGD | IPMN | HGD | 0.23 | HGD |
| 10[b] | IPMN | - | - | IPMN | LGD | 0.17 | LGD |
| 11[b] | IPMN | - | Adenocarcinoma | IPMN | HGD | 0.22 | HGD |
| 12 | IPMN | - | Carcinoma | ITPN | HGD | 0.29 | HGD |
| 13 | IPMN | 122 | HGD IPMN | IPMN | HGD | 0.26 | HGD |

[a] cysts 1 and 2 are from the same subject
[b] cysts 10 and 11 are from the same subject

FIG. 11

| Subject | MRI/CT | CEA (ng/ml) | Size (mm) | Cytology | Source of diagnosis | Diagnosis | LSS Δ | LSS diagnosis |
|---|---|---|---|---|---|---|---|---|
| 1 | IPMN | 7.8 | 11 | LGD IPMN | CD | LGD IPMN | 0.16 | LGD |
| 2 | MCN | 21 | 49 | Degenerated glandular debris | CD | Benign | 0.08 | Benign |
| 3 | Serous | 370 | 27 | Acellular specimen | CD | Benign | 0.05 | Benign |
| 4 | Pseudocyst | 7.3 | 51 | ACC or CNET | Histopathology | CNET | 0.43 | HGD/Cancer |
| 5 | IPMN | 212 | 20 | Benign paucicellular sample | CD | Benign | 0.05 | Benign |
| 6 | IPMN | 3676 | 22 | LGD IPMN | Died (cancer) | Cancer | 0.26 | HGD/Cancer |
| 7 | Serous | 226 | 32 | Negative for malignant cells | CD | Benign | 0.07 | Benign |
| 8 | IPMN | <1 | 37 | Insufficient cellular material | GCA | IPMN | 0.19 | LGD |
| 9 | IPMN | 9 | 20 | Virtually acellular specimen | GCA | IPMN | 0.25 | HGD/Cancer |
| 10 | - | 7290 | 57 | Adenocarcinoma | Cytology[a] | Cancer | 0.56 | HGD/Cancer |
| 11 | IPMN | - | 50 | Negative for malignant cells | Histopathology | Pseudocyst | 0.09 | Benign |
| 12 | - | <1 | 29 | Serous cystadenoma | GCA | Benign | 0.03 | Benign |
| 13 | Serous | - | 28 | Insufficient material | GCA | Benign | 0.08 | Benign |
| 14 | IPMN | 2364 | 21 | IPMN | GCA | LGD IPMN | 0.11 | LGD |

[a] positive predictive value (PPV) of cytology when identifying cancer is 100%[32]

```
┌─────────────────────────────┐
│ Obtain at least one spectrum, from │
│   a spatial gating probe,   │     1410
│ corresponding to light reflected │
│   from an inside surface of a │
│      pancreatic cyst        │
└─────────────────────────────┘
              │
              ▼
┌─────────────────────────────┐
│ Determining, at least from the at │
│ least one spectrum, a malignant │  1420
│ potential of the pancreatic cyst │
└─────────────────────────────┘
```

FIG. 14

METHOD AND APPARATUS TO DETERMINE THE MALIGNANT POTENTIAL OF PANCREATIC CYSTS USING LIGHT SCATTERING SPECTROSCOPY

RELATED APPLICATIONS

This Application is a national stage filing under 35 U.S.C. 371 of International Patent Application Serial No. PCT/US2018/019563, filed Feb. 23, 2018, which claims priority to U.S. Provisional Application Ser. No. 62/462,510, filed on Feb. 23, 2017, and to U.S. Provisional Application Ser. No. 62/469,982, filed on Mar. 10, 2017. The entire contents of these applications are incorporated herein by reference in their entirety.

FEDERALLY SPONSORED RESEARCH

This invention was made with government support under grant R01 EB003472 and R01 CA205431 awarded by NIH and under grant CBET-1402926, and CBET-1605116 awarded by NSF. The government has certain rights in the invention.

BACKGROUND

Pancreatic cancer has a low survival rate among all major cancers, typically six months from diagnosis. This may be due to an inability to detect it early while the cancer is still treatable, or perhaps because of the inaccessible location of the pancreas deep in the abdomen. Also, the disease often metastasizes while it is still asymptomatic.

About one fifth of pancreatic cancers arise from pancreatic cystic lesions. Yet not all lesions are precancerous, and conventional imaging tools may lack adequate accuracy to distinguish precancerous from benign cysts.

SUMMARY

In one embodiment, there is provided a spatial gating probe for performing light scattering spectroscopy on tissue, the spatial gating probe comprising: a housing; and a plurality of fiber-optic cables disposed within the housing, wherein: the plurality of fiber-optic cables comprise at least one source fiber and at least one detector fiber; the at least one source fiber is configured to emit light onto the tissue; and the at least one detector fiber is configured to receive light reflected from the tissue.

In another embodiment, there is provided an apparatus for determining a malignant potential of a pancreatic cyst, the apparatus comprising: a fixed-length tube; an endoscopic ultrasound-guided fine needle aspiration (EUS-FNA) needle disposed at an end of the fixed-length tube; and a spatial gating probe disposed within the EUS-FNA needle, the spatial gating probe comprising: a housing; and a plurality of fiber-optic cables disposed within the housing, wherein: the plurality of fiber-optic cables comprise at least one source fiber and at least one detector fiber; the at least one source fiber is configured to emit light onto the pancreatic cyst; and the at least one detector fiber is configured to receive light reflected from the pancreatic cyst.

In another embodiment, there is provided a method for determining a malignant potential of a pancreatic cyst of a patient, the method comprising: inserting a spatial gating probe into the pancreatic cyst, the spatial gating probe comprising: a housing; and a plurality of fiber-optic cables disposed within the housing, wherein the plurality of fiber-optic fibers comprise at least one source fiber and at least one detector fiber; emitting light, from the at least source fiber, onto an inside surface of the pancreatic cyst; receiving, via the at least one detector fiber, light reflected from the inside surface of the pancreatic cyst; and determining, at least from the light received via the at least one detector fiber, the malignant potential of the pancreatic cyst.

In another embodiment, there is provided at least one non-transitory computer-readable storage medium having stored thereon instructions that, when executed by at least one processor, perform a method comprising: obtaining at least one spectrum, from a spatial gating probe, corresponding to light reflected from an inside surface of a pancreatic cyst; determining, at least from the at least one spectrum, a malignant potential of the pancreatic cyst.

BRIEF DESCRIPTION OF DRAWINGS

FIG. 11 shows a table of the 13 subjects tested ex vivo.

FIG. 12 shows a table of the 14 subjects tested in vivo.

FIG. 14 shows an illustrative process flow for determining the malignant potential of a pancreatic cyst.

DETAILED DESCRIPTION

Figure 1:
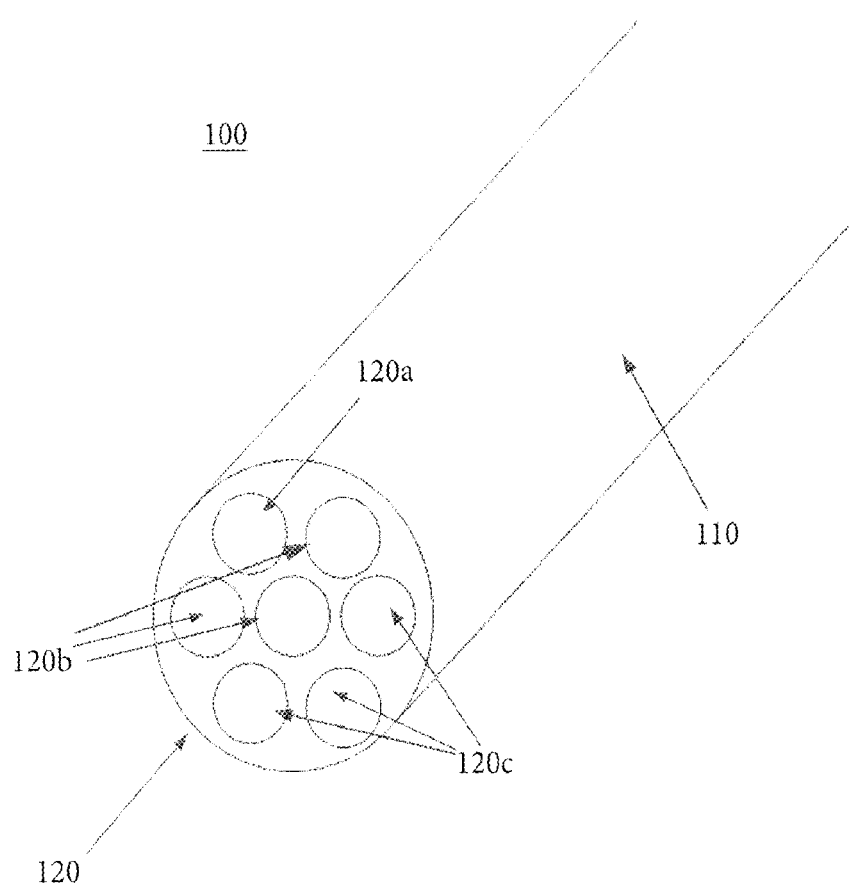
FIG. 1 shows an illustrative embodiment of a spatial gating probe.

Described herein are embodiments of an approach for predicting the malignant potential, or the potential that a cell will develop to become malignant, of pancreatic cystic lesions during routine diagnostic EUS-FNA procedures using LSS (light scattering spectroscopy). More particularly, described herein are embodiments of an approach for predicting the malignant potential of pancreatic cystic lesions with a spatial gating fiber optic probe, as well as embodiments of an approach for predicting the malignant potential of pancreatic cystic lesions with a scanning fiber probe.

Pancreatic cysts may be identified in early, treatable stages with non-invasive imaging techniques such as computed tomography (CT) and magnetic resonance imaging (MRI). Cystic lesions are relatively common, occurring in at least 2% of adults, with some studies describing the incidental finding of pancreatic cysts in more than 10% of abdominal MRIs obtained for non-pancreatic indications. However, while CT and MRI can be used to screen for the presence of cystic lesions, they have limited accuracy with regard to identifying the type of pancreatic cyst. Decisions on surgical resection of a pancreatic cyst therefore rely on EUS-FNA procedures.

There are two primary types of precancerous pancreatic cystic lesions, intraductal papillary mucinous neoplasms (IPMN), and mucinous cystic neoplasms (MCN), that may be treated surgically, achieving a high cure rate. However, the majority of cystic pancreatic lesions have no malignant potential and do not require surgery. Certain types of precancerous cysts can be safely monitored for years, and may not require surgical resection. Higher risk precancerous cysts should be removed surgically, prior to cancer development. Pancreatic surgery is complex and is associated with significant morbidity and mortality. For instance, the Whipple procedure, also known as pancreatoduodenectomy, involves removing the head of the pancreas, two thirds of the duodenum, and one third of the stomach and has a mortality rate of more than 11% when averaged over all hospitals in the US. Therefore, the decision to consider surgery for a pancreatic cyst requires the treating physician to weigh data from potentially inaccurate EUS-FNA results with several even less conclusive imaging tests and with the patient's ability to tolerate the surgery. As a result, of the pancreatoduodenectomies which are performed on cystic lesions, only about 42% are later confirmed as featuring precursor lesions with malignant potential. On the other hand, precancerous and small resectable cancerous cysts, when left untreated, have the risk of progressing to incurable cancer. There is currently no sufficiently accurate diagnostic technique that can reliably distinguish cancerous and pre-cancerous cysts from benign cysts.

A conventional technique for diagnosing the type of a pancreatic cyst involves extracting cyst fluid from the cyst during EUS-FNA procedures. The cyst fluid is then analyzed both for tissue (cytopathology) evaluation, and also for the presence of certain molecular markers or glycoproteins, such as carcinoembryonic antigen (CEA). Unfortunately, cyst fluid often contains few cells, and fluid chemical analysis lacks accuracy, perhaps resulting in dire consequences. A patient may undergo unnecessary pancreatic surgery for a benign cyst that was incorrectly diagnosed as cancerous, or a malignant cyst may be diagnosed as benign, and thus the patient does not receive surgery and develops pancreatic cancer.

Recently, a large multicenter prospective clinical study evaluated both cytology and CEA for their ability to diagnose mucinous cystic lesions based on EUS-FNA in 341 patients. Pancreatic surgical resections of 112 of these patients found that cytology of cyst fluid has a sensitivity of 35% and a specificity of 83% for diagnosing mucinous vs. non-mucinous cysts and just 22% sensitivity for detecting mucinous cystic cancers. Apart from CEA, the diagnostic potential of other molecular markers including amylase, cancer antigen (CA) 19-9, DNA, and fluid viscosity have been investigated, with CEA being the only marker that achieves enough accuracy to be of clinical utility. However, CEA addition provides only a slight improvement over cytology alone in distinguishing between benign and mucinous cysts.

Considering the high mortality and morbidity of pancreatic surgeries and the even higher mortality from untreated pancreatic cancers, there is an obvious need for the development of new diagnostic methods to accurately identify pancreatic cysts that need surgical intervention.

It has been shown that elastic light scattering can distinguish pre-cancerous and early cancerous lesions. There may be three main components of tissue light scattering spectra. The largest is a diffuse background signal from submucosal tissue, next is scattering by small organelles, and lastly a relatively small backscattered component from epithelial cell nuclei. If a beam of light is incident on an epithelial layer of tissue, a portion of the light may be backscattered from the epithelial nuclei, while the remainder may be transmitted to deeper tissue layers, where it may undergo multiple scattering. All of the diffusive light which is not absorbed in the tissue may eventually return to the surface, passing once more through the epithelium, where it may be again subject to scattering from the cell nuclei. Thus, the emerging light may consist of a large diffusive background plus the component of forward scattered and backscattered light from the nuclei of the epithelial layer.

The submucosal background may be excluded by one of various gating techniques and the smaller organelles have a very different scattering spectral dependence than that of the nuclei. Elastic light scattering can also be used to measure other cellular compartments, such as mitochondria, whose spectra are sufficiently different from that of nuclei to be distinguished. The combination of gating and difference in spectral behavior allows for the epithelial nuclear scattering spectrum to be isolated in the processed LSS signal. A significant contribution from nuclear backscattering and clear correlation of dysplasia with nuclear size has been demonstrated in earlier studies. Epithelial nuclei may be spheroidal Mie scatterers with a refractive index higher than that of the surrounding cytoplasm. Normal nuclei may have a characteristic diameter of approximately 4-7 μm. In contrast, dysplastic nuclei may be as large as 20 μm in height, occupying almost the entire cell volume. Direct comparison of the nuclear size distribution extracted from the backscattering signal to that of histological examination of the corresponding Haemotoxylin and Eosin (H&E stained) sections has also been demonstrated.

Detecting malignancies with LSS requires separating the backscattering signal coming from the epithelial cells from the multiple scattering signal coming from the underlying connective tissue. Typically, this is done using polarization gating. However, a standard aspiration needle for use in routine diagnostic EUS-FNA procedures is either 22 gauge (0.54 mm internal diameter) or 19 gauge (0.91 mm internal diameter). Such a compact package introduces difficulty in using a probe that employs polarization gating.

The inventors have recognized and appreciated a need for an approach for diagnosing pancreatic cystic lesions with improved accuracy.

Described herein are embodiments of an approach that uses LSS to solve the difficult problem of identifying pre-cancerous and early cancerous lesions in the pancreas. In some embodiments, an apparatus for diagnosing pancreatic cysts using LSS may include a needle-based LSS instrument for in vivo use during EUS-FNA procedures. In some embodiments, the needle-based LSS instrument may use spatial gating to separate the backscattering signal coming from the epithelial cells from the multiple scattering signal coming from the underlying connective tissue.

The LSS technique for identifying malignant potential of pancreatic cystic lesions during regular EUS-FNA procedure may be rapid and inexpensive, may offer great promise for distinguishing cancerous and precancerous cysts from benign cysts, and may accurately identify those pancreatic cysts that need surgical intervention. Routine use of the LSS technique may avoid unnecessary pancreatoduodenectomies and malignant cysts that otherwise could be missed may be identified.

FIG. 1 shows an illustrative embodiment of a spatial gating probe 100. In some embodiments, the spatial gating probe 100 includes a housing 110. The housing 110 may be made of a robust medical grade biocompatible polyimide, although other suitable materials are possible. In some embodiments, the spatial gating probe 100 may include a plurality of fiber-optic cables 120 disposed within the housing 110. The plurality of fiber-optic cables may have a numerical aperture (NA) of approximately 0.21, and may each have a diameter of approximately 100 μm. In some embodiments, the plurality of fiber-optic cables 120 may comprise at least one source fiber 120a, at least one first detector fiber 120b, and at least one second detector fiber 120c. The at least one source fiber 120a may be configured to emit light onto a surface of a tissue. In the embodiment illustrated in FIG. 1, the at least one source fiber 120a is configured to emit light in a direction parallel to the housing 110. However, it should be appreciated that the at least one source fiber 120a may be configured to emit light in other directions, for example in a direction perpendicular to the housing 110. The at least one first detector fiber 120b and the at least one second detector fiber 120c may be configured to receive light scattered from the tissue. In some embodiments, the tissue is tissue from a pancreatic cyst.

In some embodiments, the plurality of fiber-optic cables 120 may be arranged in a hexagonal shape. In such an embodiment, the at least one source fiber 120a may be located on an outer edge of the hexagonal shape. The at least one first detector fiber 120b may be disposed at a first distance from the at least one source fiber 120a, and the at least one second detector fiber 120c may be disposed at a second distance from the at least one source fiber 120a. In some embodiments, the second distance may be greater than the first distance. The second distance may be equal to approximately 240 μm and the first distance may be equal to approximately 120 μm.

Figure 2:
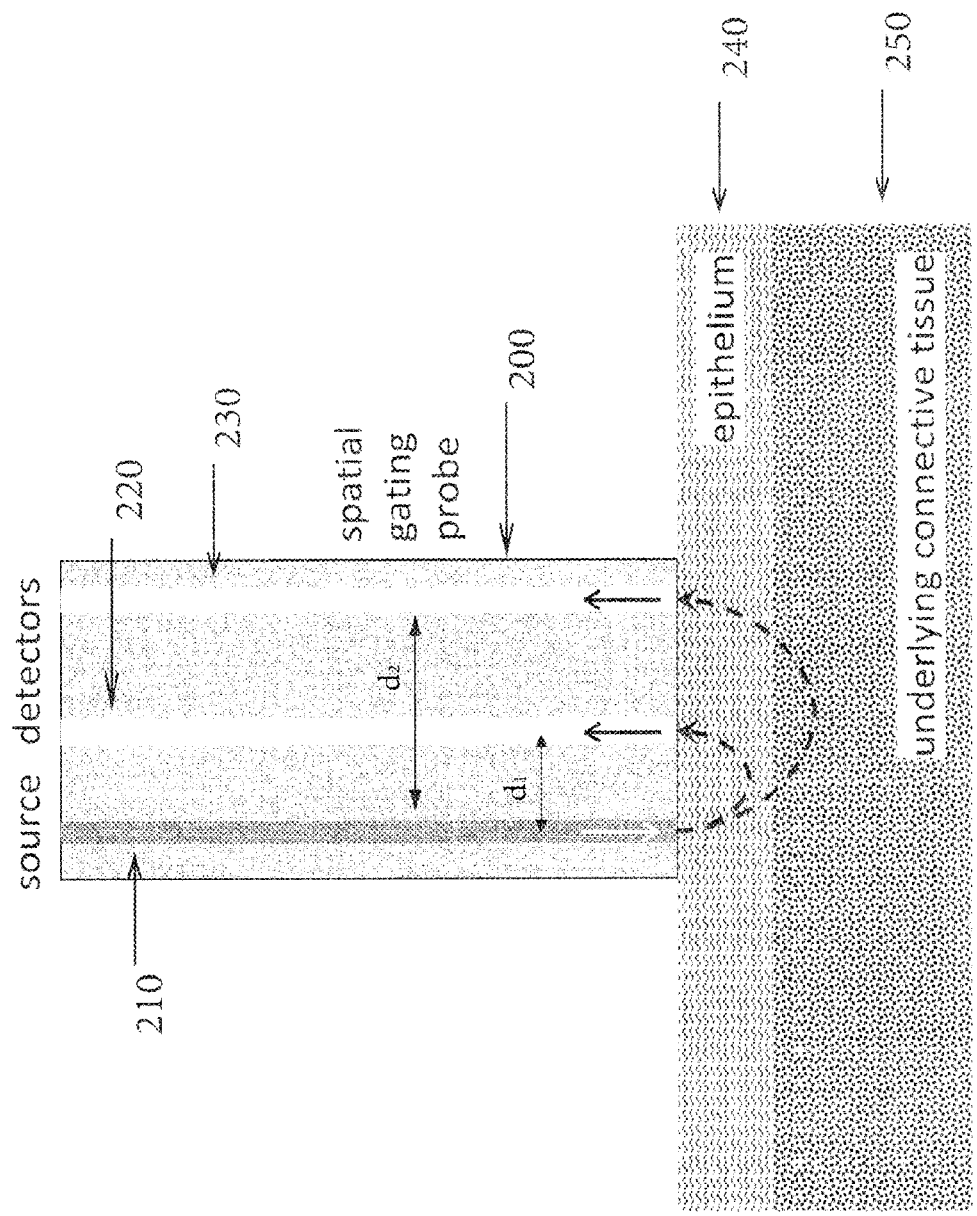
FIG. 2 shows an illustrative embodiment of a system in which a spatial gating probe may obtain LSS measurements.

FIG. 2 shows an illustrative embodiment of a system in which a spatial gating probe 200 may obtain LSS measurements. The spatial gating probe 200 may include at least one source fiber 210 (e.g., the at least one light source fiber 120a of FIG. 1) through which a light source may provide light. In some embodiments, the light source may be a broadband light source, and may be an arc lamp. The at least one source fiber 210 may be configured to emit light onto a tissue, for example a pancreatic cyst. In some embodiments, the tissue may include an epithelium layer 240 and underlying connective tissue 250. The spatial gating probe 200 may include at least one first detector fiber 220 (e.g., the at least one first detector fiber 120b of FIG. 1), disposed at a distance $d_1$ from the source fiber 210. The spatial gating probe 200 may also include at least one second detector fiber 230 (e.g., the at least one second detector fiber 120c of FIG. 1), disposed at a distance $d_2$ from the source fiber 210. The at least one first detector fiber 220 and the at least one second detector fiber 230 may be configured to receive light scattered from the tissue.

The at least one first detector fiber 220 may obtain a first spectrum corresponding to light emitted from the at least one source fiber 210, reflected by the tissue, and detected by the at least one first detector fiber 220. The at least one second detector fiber 230 may obtain a second spectrum corresponding to light emitted from the at least one source fiber 210, reflected by the tissue, and detected by the at least one second detector fiber 230. Because the at least one second detector fiber 230 may be disposed at a larger distance from the at least one source fiber 210 than is the at least one first detector fiber 220, the at least one second detector fiber 230 may receive light that penetrated deeper into the tissue than the light received at least one first detector fiber 220. In some embodiments, the light received by the at least one first detector fiber 220 may penetrate only into the epithelium layer 240, and the light received by the at least one second detector fiber 240 may penetrate into both the epithelium layer 240 and the underlying connective tissue 250.

It may be ideal to isolate light reflected by just the epithelium layer 240, as light reflected by the epithelium layer 240 may be most relevant for diagnosing the malignancy of the tissue. In some embodiments, the second spectrum obtained by the at least one second detector fiber 230 may be subtracted from the first spectrum obtained by the at least one first detector fiber 220. By doing so, the spectrum of light reflected by just the epithelium layer 240 may be isolated. This way, the tissue surface may be analyzed for malignancy, as cancerous and precancerous cells produce different spectra than do noncancerous cells.

In some embodiments, the tissue may be tissue from a pancreatic cyst, and the epithelium layer 240 and underlying connective tissue 250 may be from the pancreatic cyst. In such an embodiment, the spatial gating probe 200 may be utilized to determine the malignant potential of the pancreatic cyst. While FIG. 2 shows the spatial gating probe 200 in contact with the tissue, specifically the epithelium layer 240, it should be appreciated that other arrangements are also possible, for example an arrangement where the spatial gating probe 200 is disposed at a distance from the tissue.

Figure 3:
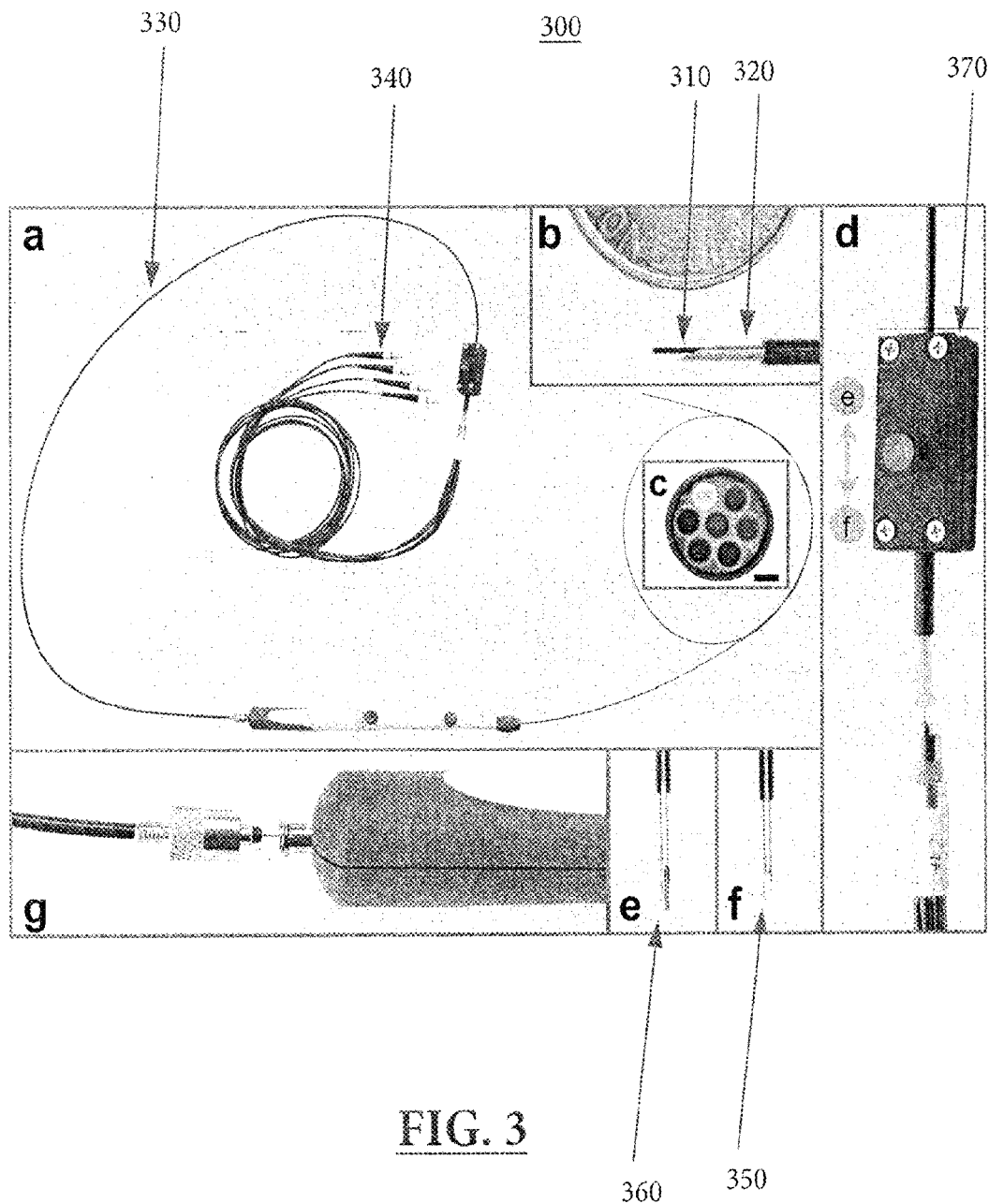
FIG. 3 shows an illustrative embodiment of an apparatus for determining the malignant potential of a pancreatic cyst.

FIG. 3 shows an illustrative embodiment of an apparatus 300 for diagnosing pancreatic cysts. In some embodiments, the apparatus 300 may include a spatial gating probe 310 (e.g., the spatial gating probe 100 of FIG. 1 or the spatial gating probe 200 of FIG. 2) that may be disposed in an FNA needle 320. In some embodiments, the spatial gating probe 310 may be disposed on one end of a fixed-length tube 330. The apparatus may also include four SubMiniature Version A (SMA) connectors 340 on another end, opposite the spatial gating probe 310, of the fixed-length tube 330. Three of the four SMA connectors 340 may be configured to couple groups of detector fibers of the spatial gating probe 310, with 120 μm, 220 μm, and 240 μm distal end source-detector separations, with at least one spectrometer. The fourth SMA connector 340 may be configured to couple a source fiber of the spatial gating probe 310 with a broadband light source.

In some embodiments, the spatial gating probe 310 may comprise multiple fiber-optic cables, as seen in 3(c). The multiple fiber-optic cables may be arranged in a hexagonal pattern. One of the outer fiber-optic cables may be selected as a source fiber, and may be connected to a dedicated SMA connector 340. The source fiber may be the fiber-optic cable through which the broadband light source may provide light. The other fiber-optic cables may be detector fibers and may be arranged around the light source fiber such that three of the detector fibers are a first distance away from the light source fiber, and three of the detector fibers are a second distance away from the light source fiber. The detector fibers may be connected to other SMA connectors 340 coupled to at least one spectrometer. In some embodiments, the first distance may be 120 μm and the second distance may be 240 μm. The close distance between the light source fiber and detector fibers may allow for the light to only penetrate up to a depth of a few hundred micrometers in tissue onto which the light is being emitted. In doing so, the spatial gating probe 310 may be able to more effectively isolate the light scattered by an epithelial layer of the tissue, which may be most relevant for diagnosing the malignancy of the tissue.

In some embodiments, the spatial gating probe 310 may be able to extend beyond the beveled tip of the FNA needle 320. In some embodiments, the spatial gating probe may extend 2 mm beyond the beveled tip of the FNA needle 320. In a first state 350, the spatial gating probe 310 may not extend beyond the tip of the FNA needle 320. In the first state 350, the spatial gating probe 310 may be protected while the FNA needle 320 is being inserted into the patient. In a second state 360, the spatial gating probe 310 may extend beyond the tip of the FNA needle 320. In the second state 360, the spatial gating probe 310 may be able to take unprohibited measurements.

In some embodiments, the apparatus may include a probe latching mechanism 370. The probe latching mechanism 370 may allow for the position of the spatial gating probe 310 to be locked with a position locking button, and toggled to extend or retract the probe tip from the needle. For example, the probe latching mechanism 370 may control whether the spatial gating probe 310 is in the first state 350 or in the second state 360. The probe latching mechanism 370 may also be configured to lock the spatial gating probe 310 in the first state 350 or in the second state 360. The probe latching mechanism 370 may have a Luer lock connection for attaching it to a metal ferrule of the spatial gating probe 310. The other side may be attached to the fixed-length tube 330. In some embodiments, the fixed-length tube 330 may be locked on a needle handle with a Luer lock connection.

In some embodiments, the probe may be connected to an optical spectroscopy clinical system. In such embodiments, the source fiber of the spatial gating probe 310 may be coupled to a 75W Xenon arc lamp source (Apex, Newport), and the receiver fibers of the spatial gating probe 310 may be coupled to fiber optic spectrometers (AvaSpec, Avantes).

Figure 4:
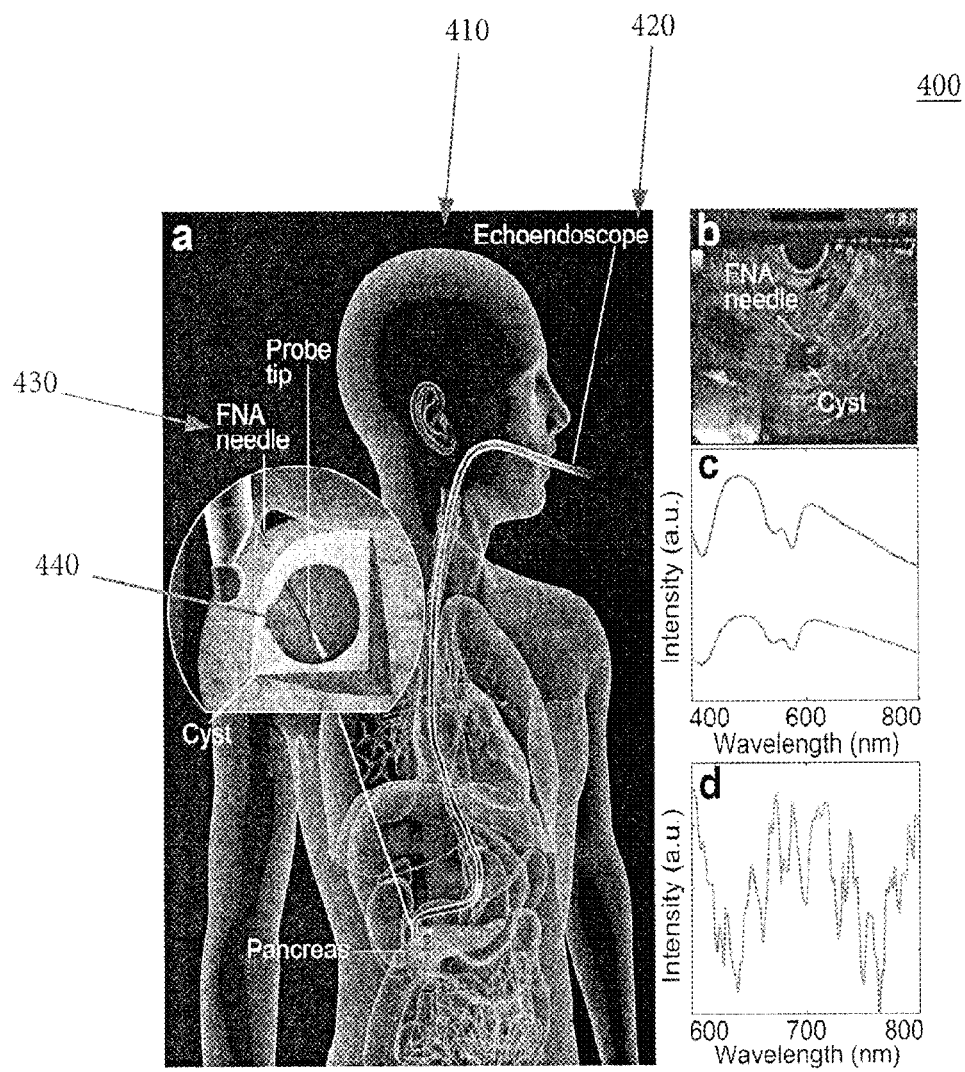
FIG. 4 shows an illustrative embodiment of a system in which an apparatus for determining the malignant potential of a pancreatic cyst may be employed.

FIG. 4 shows an illustrative embodiment of a system 400 in which an apparatus for diagnosing pancreatic cysts may be employed. In some embodiments, a patient 410 may be administered sedation and supplemental oxygen may be used. An echoendoscope 420 may be introduced through the mouth of the patient 410 and advanced to the patient's duodenum. After pancreatic EUS examination, an FNA needle 430 may be inserted into the echoendoscope 420, and a cyst may be punctured under ultrasound guidance. In some embodiments, a spatial gating probe 440 may be extended beyond the tip of the FNA needle 430 with a probe latching mechanism and locked into that position with a locking button. By moving and/or changing an angle of orientation the spatial gating probe 440 slightly, multiple spatially gated LSS measurements may be obtained of locations on the internal cyst surface (e.g. from 7 to 31 locations), covering a portion of the forward hemisphere of the internal cyst surface under EUS guidance. The number of locations measured may be dependent on the size of the cyst. FIG. 4b shows an EUS image of the FNA needle penetrating a pancreatic cyst with a spatial gating probe inserted.

FIG. 4c shows typical spectra collected in the cyst from detector fibers in one embodiment of a spatial gating probe. The upper line shows a spectrum collected from a detector fiber at a distance of 120 μm from a source fiber of the spatial gating probe. The lower line shows a spectrum collected from a detector fiber at a distance of 240 μm from the source fiber. FIG. 4c shows just the backscattering component obtained from the spectra at both 120 μm and 240 μm detector fibers. The backscattering component may be obtained by subtracting the spectrum obtained from the detector fiber 240 μm from the source fiber from the spectrum obtained from the detector fiber 120 μm from the source fiber. In this way, light scattered by an epithelial layer of the pancreatic cyst of the patient 410 may be isolated, and the pancreatic cyst's malignant potential may be determined.

Figure 5:
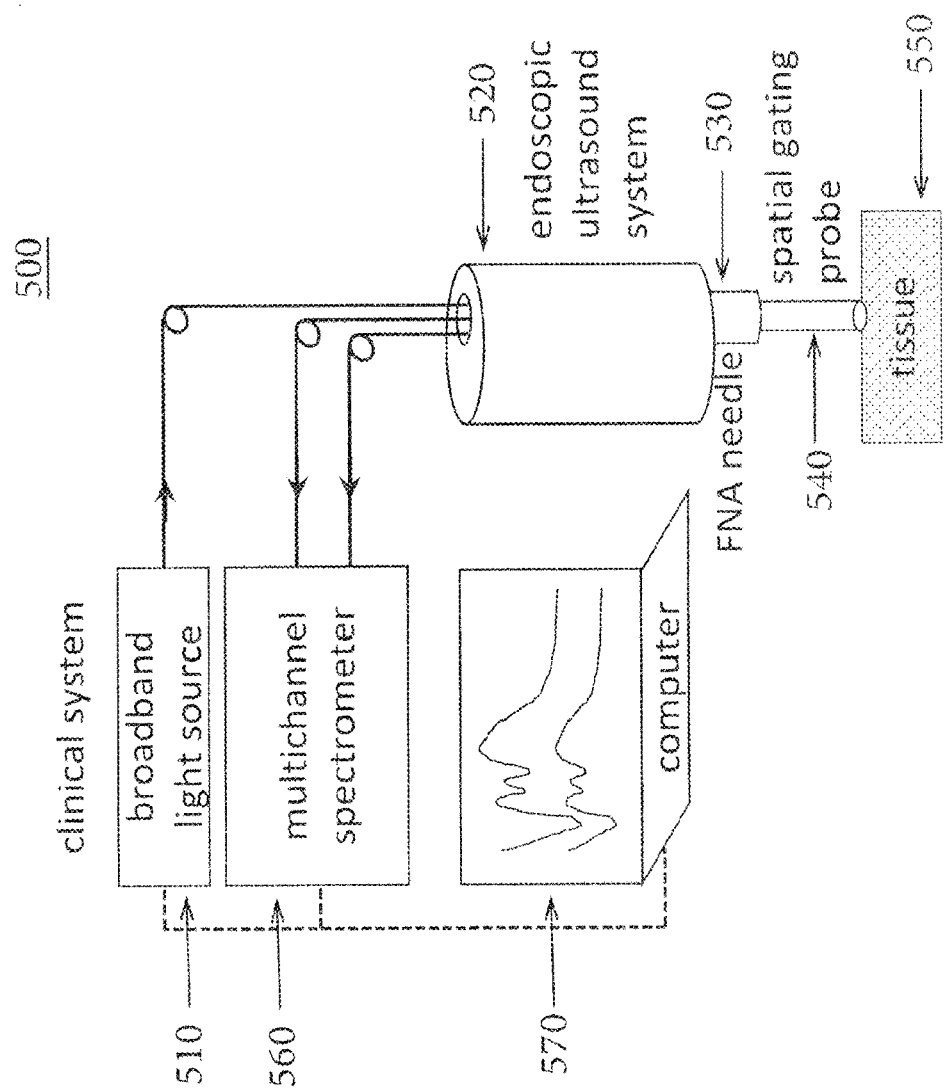
FIG. 5 shows an illustrative embodiment of a system for determining the malignant potential of a pancreatic cyst may be employed.

FIG. 5 shows an illustrative embodiment of a system 500 in which an apparatus for diagnosing the malignant potential of pancreatic cysts may be employed. In some embodiments, the system 500 may include a broadband light source 510, an endoscopic ultrasound system (EUS) 520, an FNA needle 530, a spatial gating probe 540, tissue 550, at least one multichannel spectrometer 560, and a computer 570. In some embodiments, the spatial gating probe 540 may be inserted in the FNA needle 530 guided by the endoscopic ultrasound system 520. The broadband light source 510 may be provided to a source fiber of the spatial gating probe 540, and the spatial gating probe 540 may be configured to take LSS measurements of the tissue 550. In some embodiments, the tissue 550 is tissue of a pancreatic cyst, and the spatial gating probe 540 is configured to take LSS measurements of the tissue of the internal surface of the pancreatic cyst. In some embodiments, the broadband light source 510 may be an arc lamp.

The spatial gating probe 540 may include a plurality of detector fibers, (e.g. the at least one first detector fiber 120b and the at least one second detector fiber 120c in FIG. 1) may be coupled to a respective Cable Management Arm (CMA) connector, which may then be coupled to the at least one multichannel spectrometer 560. The multichannel spectrometer 560 may be connected to the computer 570, on which spectra obtained by the detector fibers of the spatial gating probe 540 may be analyzed. For example, the computer 570 may analyze a first spectrum obtained by the at least one first detector fiber and a second spectrum obtained by the at least one second detector fiber of the spatial gating probe 540. The computer 570 may subtract the second spectrum from the first spectrum in order to isolate light reflected by the epithelium layer of the tissue 550. In this way, the cells of the epithelial layer of the tissue 550 may be analyzed and an accurate diagnosis of the malignant potential of the cells may be obtained.

To obtain an accurate diagnosis, the system may obtain a diagnostic parameter $\Delta$. This may be performed on the computer 570, as shown in FIG. 5. In order to obtain the diagnostic parameter $\Delta$, the computer 570 may utilize the fact that the contribution of backscattering to the total spatially resolved reflectance decreases with the increase in separation r between the source fiber and the detector fibers of the spatial gating probe 540 (e.g. the separation between the at least one source fiber 120a, and the at least one first detector fiber 120b and the at least one second detector fiber 120c of FIG. 1), significantly faster than that of the multiple scattering signal. While total reflectance may be calculated as a sum of the diffuse reflectance and single large angle backscattering for the closest detector fiber, it may also be accurately approximated with the diffuse reflectance from the farthest one alone.

The diagnostic parameter $\Delta$ may be used to make a determination of the malignant potential of tissue, for example of a pancreatic cystic lesion. If the diagnostic parameter Δ is less than 0.1, the tissue may be classified as benign. If the diagnostic parameter Δ is greater than or equal to 0.1 and less than 0.2, the tissue may be classified as low-grade dysplasia (LGD). If the diagnostic parameter Δ is greater than or equal to 0.2, the tissue may be classified as high-grade dysplasia (HGD). The thresholds Δ=0.1 and Δ=0.2 may correspond to 25% and 50% enlarged nuclei in measured cells of the tissue. While thresholds of Δ=0.1 and Δ=0.2 may be used, it should be appreciated that other thresholds may be used in order to classify the tissue.

In the 600 nm to 800 nm wavelength range, tissue absorption may be ignored and the diffuse reflectance for a detector fiber i may be written as $$R_i^d[\mu_s'(\lambda)] = \frac{1}{\pi^2 r_s^2 r_i^2} \int_{A_s} dA_s \int_{A_i} dA_i R^d[\mu_s'(\lambda)|r_s - r_i|]$$

where $R^d$ is the diffuse reflectance density. The integrals here may be numerically calculated over the area of the light source fiber $A_s$, with radius $r_s$, and detector fibers $A_i$ with radii $r_i$ (I=1, 2).

Therefore, utilizing spectral measurements $S_1(\lambda)$ and $S_2(\lambda)$ by collection fibers 1 and 2, respectively, the following system of equations $$R_1^d[\mu_s'(\lambda)] + R^b(\lambda) = S_1(\lambda)$$

$$R_2^d[\mu_s'(\lambda)] = S_2(\lambda)$$

may be obtained, where $R^b(\lambda)$ is the single large angle backscattering component. This component carries diagnostic information and has been previously evaluated from polarization gated data.

The system may be calibrated by using phantom experiments to isolate $R^b(\lambda)$ by removing the multiple scattering contribution in the system of equations. This contribution, in the case of weak absorption, may have the same spectral dependence for both fibers. This can be understood by considering that multiple scattering is primarily dependent on the reduced scattering coefficient $\mu_s'(\lambda)$ near the point of entry. Therefore, using phantom experiments, the multiple scattering component may be calibrated in multiple detector fibers to ensure that it can be cancelled. In some embodiments, phantom experiments with scattering coefficients close to that of tissue from 0.5 μm and 0.99 μm diameter polystyrene beads (Polysciences) in agarose gel (Sigma) may be measured.

Figure 6:
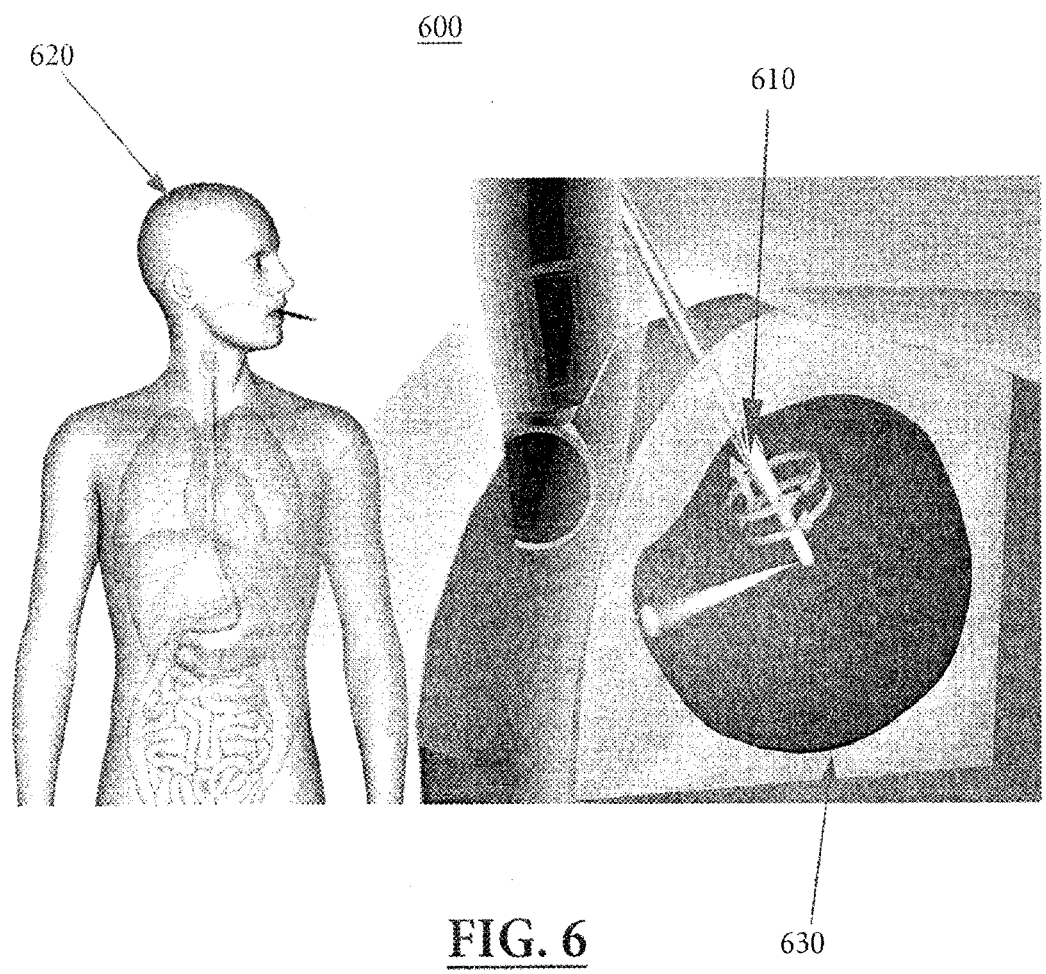
FIG. 6 shows an illustrative embodiment of a system in which an apparatus for determining the malignant potential may of a pancreatic cyst may be employed.

FIG. 6 shows an illustrative embodiment of a system 600 in which an apparatus for determining the malignant potential may of a pancreatic cyst may be employed. In some embodiments, the system 600 may be similar to the system 400 (shown in FIG. 4), wherein a spatial gating probe 610 may be inserted into a pancreatic cyst 630 of a patient 620 through an FNA needle. In the embodiment shown in FIG. 6, the spatial gating probe 610 (more specifically, at least one source fiber of the spatial gating probe 610) may be configured to emit light in a direction perpendicular to a housing of the spatial gating probe 610. The spatial gating probe 610 may be configured to rotate, such that the spatial gating probe 610 may take measurements in a 360 degree rotation within the pancreatic cyst 630.

A number of translational steps and variable step size of a linear scan may be determined based on a size of the pancreatic cyst 630 in order to ensure 30% overlap of adjacent measurement locations, and an even coverage of the entire internal surface of the pancreatic cyst 630. In some embodiments, the illumination beam may be slightly divergent, and thus a number of angular steps may be independent of the size of the pancreatic cyst 630. In some embodiments, the spatial gating probe 610 may include a lens configured to collimate the light emitted from the spatial gating probe 610. While scanning, each 360 degree clockwise rotation of the spatial gating probe 610 may be followed by a linear retraction step and a 360 degree counterclockwise rotation. In the embodiment shown in FIG. 6, the spatial gating probe 610 may perform optical biopsy on approximately 800 sites in a 3 cm diameter pancreatic cyst, interrogating the entire internal cyst surface in approximately 30 seconds. After scanning, the spatial gating probe 610 may be removed from the FNA needle.

Figure 7:
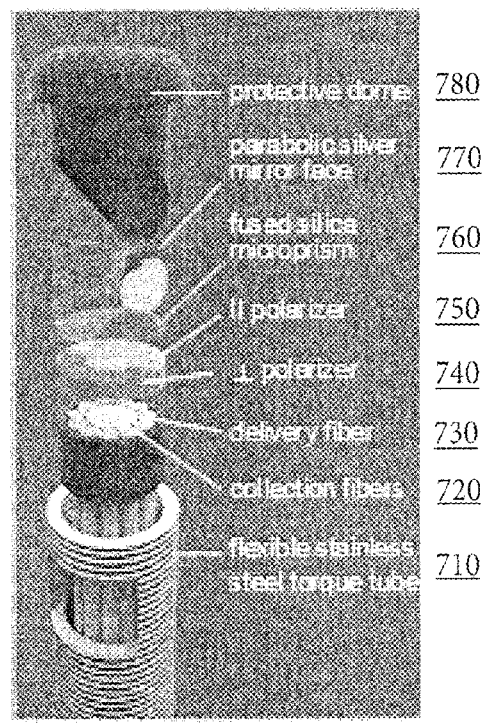
FIG. 7 shows an exploded view of an embodiment of a spatial gating probe.

FIG. 7 shows an exploded view of an embodiment of a spatial gating probe 700. The spatial gating probe 700 may be similar to the spatial gating probe 610 (shown in FIG. 6), and me be configured to emit light in a direction perpendicular to a housing of the spatial gating probe 700. The spatial gating probe 700 may include a torque tube 710 (made out of, for example, flexible stainless steel), at least one collection fiber 720, at least one delivery fiber 730, at least one orthogonal polarizer 740, at least one linear polarizer 750, at least one lens, for example microprism 760 (made out of, for example, fused silica), a parabolic silver mirror face 770, and a protective dome 780. The spatial gating probe 700 may be able to fit into a EUS-FNA needle and be capable of quickly scanning an internal surface of a pancreatic cyst.

Light from a Laser-Driven Light Source may be coupled into the at least one delivery fiber 730 which may be attached to the at least one linear polarizer 750 with the at least one orthogonal polarization component 740. In some embodiments, the at least one delivery fiber 730 may be 200 μm and the cylindrical linear polarizer/analyzer may be 100 μm thick and may have a 480 μm diameter. The at least one deliver fiber 730 may be surrounded by twelve collection fibers 720 combined in two groups. The collection fibers may be 100 μm. Each group of collection fibers 720 may be behind a linear polarizer 750, which may be shaped to ensure that one group collects light with the same polarization as the delivery fiber 730 and the other collects perpendicularly polarized light.

The microprism 760 may have a silver parabolic face and may be mounted on the polarizers 740 and 750 to partially collimate light and direct it to the cyst wall. This geometry may minimize the effect of varying distance between the probe tip and the tissue surface. Light from the microprism 760 may pass through the face perpendicular to the polarizers 740 and 750 at an oblique angle to the spatial gating probe 700 to avoid glass/fluid boundary reflection and light reflected from the tissue may follow the reverse path to the collection fibers 720. An apex of the microprism 760 may be capped with a solid protective dome. A single design element with a single refractive surface and an optically polished, low-scatter mirror may greatly reduce stray light while improving collimation and overlap of the delivery and collection beams. The resulting increase in signal-to-noise ratio (SNR) of the apparatus may facilitate faster scanning speeds and more accurate spectral characteristics. An outer surface of the spatial gating probe 700 may be a medical-grade flexible polytetrafluoroethylene coated stainless steel torque tube (Creganna Medical) that may translate rotary and linear scanning via the control box with two stepper motors. In some embodiments, the internal diameter of the torque tube 710 may be 490 μm and the outside diameter may be 660 μm, making it compatible with commercially available 19-gauge EUS-FNA needles.

Figure 8:
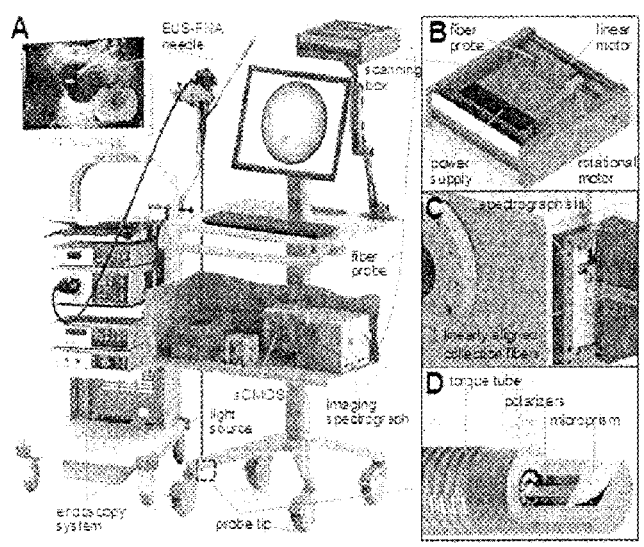
FIG. 8 shows an illustration of an embodiment of an apparatus for diagnosing pancreatic cysts.

FIG. 8 shows an illustration of an embodiment of an apparatus 800 for diagnosing pancreatic cysts. The probe may employ a broadband Laser-Driven Light Source (LDLS) which may use a continuous-wave (CW) laser to directly heat Xenon plasma to high temperatures and allow efficient fiber coupling with high brightness and stability in a relatively compact form. The apparatus may include a scanning control box which may rotate and retract the scanning fiber probe with rotational (DT-34, Plmicos) and linear (Micro Stage MTS-70) stepper motors. The motors may provide three revolutions of the scanning fiber probe per second and 3 mm per second of linear motion, enabling the duration of data collection for an average size pancreatic cyst to be less than 30 seconds. The scanning control box may be operated with a custom LabVIEW software interface, which may synchronize the scanning of illumination fibers in the scanning fiber probe with spectrometer data capture.

At a proximal end of the scanning fiber probe, collection fibers may be arranged in a line and coupled to an imaging spectrograph (Acton SP-2300i, Princeton Instruments) and a cooled high-speed scientific Complementary Metal Oxide Semiconductor (CMOS) camera (sCMOS, Andor). The scanning fiber probe may include 12 collection fibers, which may be mapped into a liner arrangement in a ferrule, which may then be aligned with a spectrograph slit. Relay optics may then map each fiber to a non-overlapping region with multiple pixels (e.g. 31 pixels).

Figure 9:
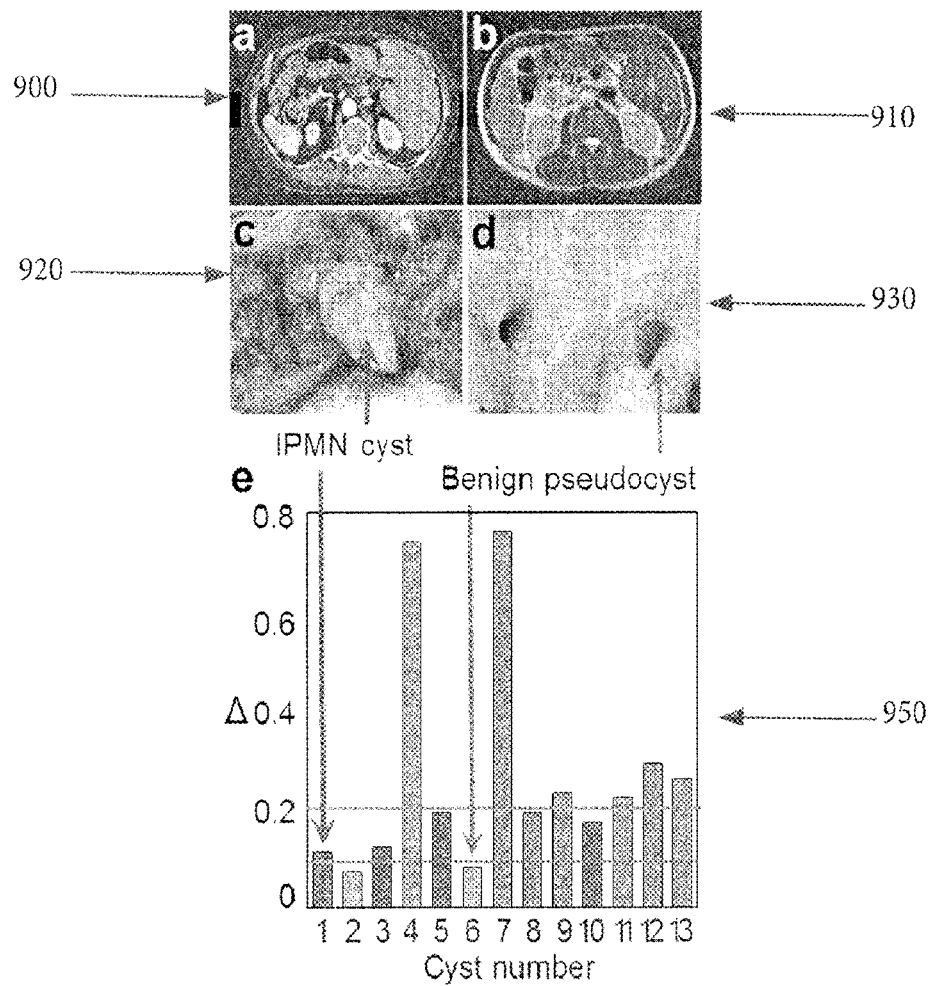
FIG. 9 shows an example of optical spectroscopic differentiation of cystic neoplasms for testing done on 13 subjects ex vivo.

FIG. 9 shows an example of optical spectroscopic differentiation of cystic neoplasms for testing done on 13 subjects ex vivo. For this testing, LSS measurements were polarization gated, rather than spatially gated as, since testing was done ex vivo and the probe was not fed through an FNA needle, there was no size requirement and the spatially gated probe was not needed. Image 900 shows an abdominal and pelvic CT angiography of a first subject. Image 920 shows a cross sectional cut photograph of a corresponding pancreatic sample of the first subject, with cysts clearly seen. The first subject had a 1.3 cm×2.3 cm cystic lesions within the pancreatic tail, which was detected via abdominal and pelvic CT angiography and described as a possible size-branch IPMN. EUS-FNA cyst fluid resulted in a CEA of 686 ng/ml, significantly higher than the 192 ng/ml cut-off suggestive of a mucinous lesion. Though the CEA level and cytology results were inconclusive for cancer, these results, along with the size of the cyst and clinical findings, were considered worrisome enough to warrant pancreatic surgery. LSS spectroscopy performed on the freshly resected cyst diagnosed all 7 locations within the cyst as LGD (low-grade dysplasia) and later postoperative histopathology findings for all 7 locations were indeed IPMN with LGD. Image 910 shows a magnetic resonance colangiopancreatography (MRCP) in a second subject. Image 930 shows a cross sectional cut photograph of a corresponding pancreatic sample with cysts clearly seen. In this example, the diagnostic parameter Δ for the second subject corresponded to a diagnosis of a benign cyst.

Graph 950 shows the results of this testing. When the diagnostic parameter Δ was taken into account, 2 benign cases, 4 LGD cases, and 6 HGD (high-grade dysplasia) cases were correctly identified, while one HGD case was identified as LGD.

Figure 10:
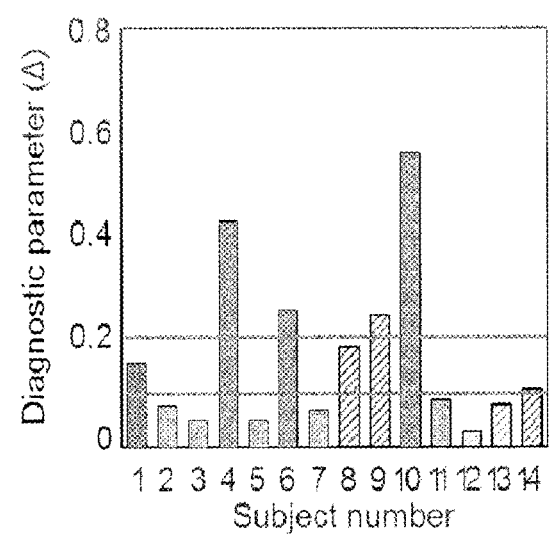
FIG. 10 shows an example of optical spectroscopic differentiation of cystic neoplasms for testing done on 14 subjects in vivo.

FIG. 10 shows an example of optical spectroscopic differentiation of cystic neoplasms for testing done on 14 subjects in vivo. This testing was done with a spatial gating probe as the use of EUS-FNA required a probe with a reduced size. The solid bars represent a diagnostic gold standard, obtained from postoperative/postmortem histopathology or survival with follow-ups. Untreated cystic malignancy has a median survival of 3 months and a one-year survival rate of less than 10%. Thus, a one-year follow-up after LSS measurement would identify the vast majority of previously undetected malignancies due to the rapid progression of the disease. Within the 14 subjects shown in FIG. 8, two had definitive histopathology diagnoses, one was classified by our technology as cancer but misdiagnosed by cytology as negative for malignancy and the patient has died of metastatic cancer, one had definitive adenocarcinoma cytology diagnosis (though cytology has poor sensitivity it is very accurate when identifying cancer), and five have survived for more than one year with follow-ups showing no evidence of malignancy. We consider the diagnosis of these 9 patients as reliable according to the above gold standard.

According to the Subject number, subjects 4, 6, and 10 represent adenocarcinoma or a cystic neuroendocrine tumor (CNET), subject 1 represents LGD IPMN, and subjects 2, 3, 5, 7, and 11 represent benign. The striped bars represent the diagnostic secondary endpoint of an independent consensus assessment of the cysts by two expert gastroenterologists. Subjects 12 and 13 and subjects 8, 9, and 14 represent LGD and HGD/Cancer diagnostic algorithm cut-offs, respectively.

FIG. 11 shows a table of the 13 subjects tested ex vivo. The table shows the polarization gated LSS optical spectroscopic technique vs. MRI/CT, CEA level, preoperative cytology, and postoperative histopathology. The two last columns present the diagnostic parameter Δ and the LSS diagnosis. MRI includes both abdominal MRI and MRCP. In the table, ITPN refers to intraductal tubulopapillary neoplasm. Empty cells represent no information due to lack of imaging classification, cellular material, or absence of data on CEA level.

FIG. 12 shows a table of the 14 subjects tested in vivo. The table shows the spatially gated LSS optical spectroscopic technique vs. MRI/CT, CEA level, cyst size, cytology, and the resulting diagnosis. The source of the resulting diagnosis is either histopathology, gastroenterologists' consensus assessment (GCA), or conclusive diagnosis (CD), combining more than one-year follow-up with GCA. The two last columns present the diagnostic parameter Δ and the LSS diagnosis. MRI includes both abdominal MRI and MRCP. In the table, ACC refers to acinar cell carcinoma. Empty cells represent no information due to lack of imaging classification or absence of data on CEA level.

Figure 13:
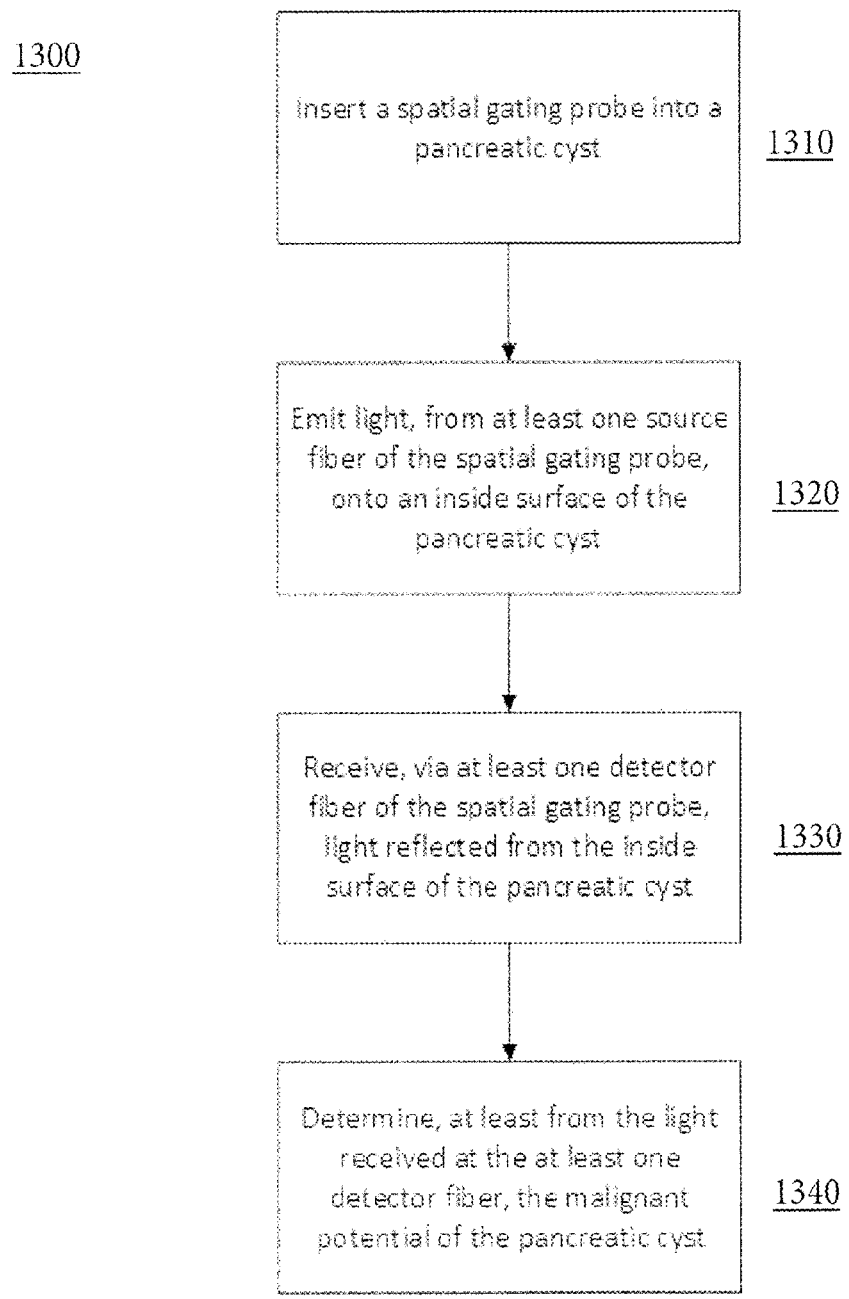
FIG. 13 shows an illustrative process flow for determining the malignant potential of a pancreatic cyst.

FIG. 13 shows an illustrative process flow 1300 for determining the malignant potential of a pancreatic cyst. The process flow 1300 may be executed with a system including a spatial gating probe as described herein. The process flow 1300 may include a step 1310, in which the spatial gating probe is inserted into the pancreatic cyst. The process flow 1300 may then include a step 1320, in which at least one source fiber, of the spatial gating probe, emits light onto an inside surface of the pancreatic cyst. The process flow 1310 may then include a step 1330, in which at least one detector fiber, of the spatial gating probe, receives light reflected from the inside surface of the pancreatic cyst. The process flow 1300 may then include a step 1340, in which the malignant potential of the pancreatic cyst is determined at least from the light received at the at least one detector fiber. It should be appreciated that the process flow 1300 is not limited to the steps shown in FIG. 13, as it is shown for illustrative purposes only. The process flow 1300 may include additional steps, such as inserting an FNA needle into the pancreatic cyst, and extending the spatial gating probe beyond the tip of the FNA needle.

FIG. 14 shows an illustrative process flow 1400 for determining the malignant potential of a pancreatic cyst. The process flow 1400 may be executed by a computer included in a system with a spatial gating probe as described herein. The process flow 1400 may include a step 1410, in which at least spectrum, corresponding to light reflected from an inside surface of a pancreatic cyst, is obtained from the spatial gating probe. The process flow 1400 may then include a step 1420, in which the malignant potential of the pancreatic cyst is determined, at least from the at least one spectrum. It should be appreciated that the process flow 1400 is not limited to the steps shown in FIG. 14, as it is shown for illustrative purposes only. The process flow 1400 may include additional steps, such as determining a diagnostic parameter Δ, comparing the diagnostic parameter Δ to at least one threshold, and classifying the pancreatic cyst based on at least the comparison.

Figure 15:
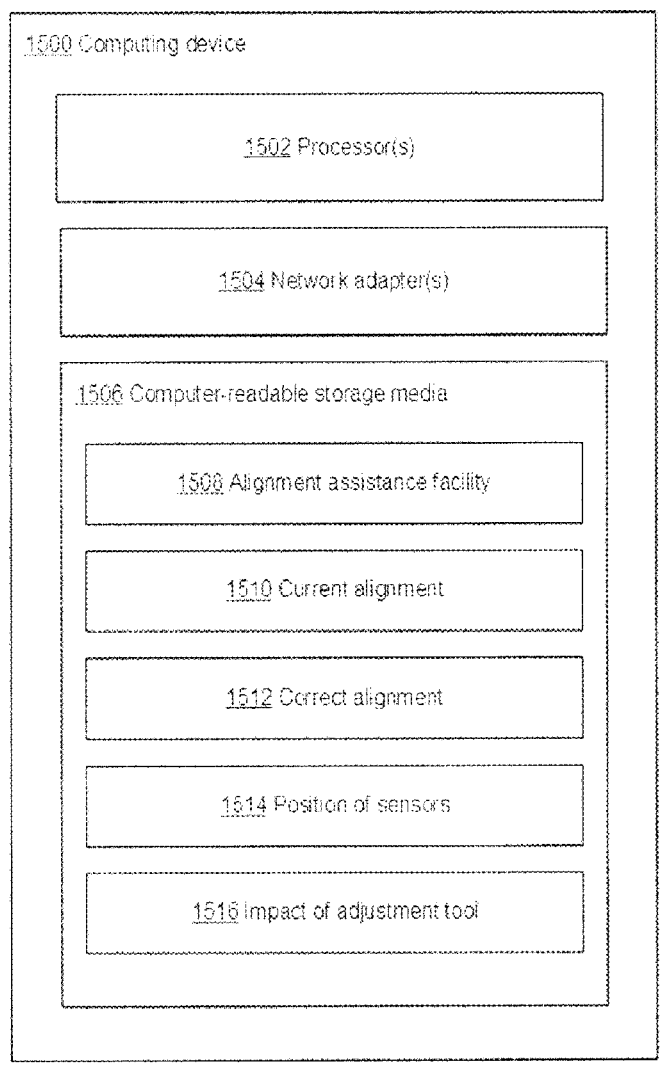
FIG. 15 illustrates an embodiment of a computing device for receiving and analyzing signals in a system for determining the malignant potential of tissue, for example of a pancreatic cyst.

FIG. 15 illustrates an embodiment of a computing device 1500 for receiving and analyzing signals in a system for determining the malignant potential of tissue, for example of a pancreatic cyst. For example, the computing device 1500 may be included in the system 500 (shown in FIG. 5), for example as the computer 570. In one embodiment, the computing device 1500 may include at least one processor(s) 1502 and at least one network adapter(s) 1504. The computing device may also include computer readable storage media 1506 which may include an alignment assistance facility module 1508, a current alignment module 1510, a correct alignment module 1512, a position of sensors module 1514, and an impact of adjustment tool module 1516. The computing device 1500 may be designed to receive and analyze signals from a system utilizing a method for determining the malignant potential of a pancreatic cyst as described herein.

Techniques operating according to the principles described herein may be implemented in any suitable manner. Included in the discussion above are a series of flow charts showing the steps and acts of various processes that determine the malignant potential of a pancreatic cyst. The processing and decision blocks of the flow charts above represent steps and acts that may be included in algorithms that carry out these various processes. Algorithms derived from these processes may be implemented as software integrated with and directing the operation of one or more single- or multi-purpose processors, may be implemented as functionally-equivalent circuits such as a Digital Signal Processing (DSP) circuit or an Application-Specific Integrated Circuit (ASIC), or may be implemented in any other suitable manner. It should be appreciated that the flow charts included herein do not depict the syntax or operation of any particular circuit or of any particular programming language or type of programming language. Rather, the flow charts illustrate the functional information one skilled in the art may use to fabricate circuits or to implement computer software algorithms to perform the processing of a particular apparatus carrying out the types of techniques described herein. It should also be appreciated that, unless otherwise indicated herein, the particular sequence of steps and/or acts described in each flow chart is merely illustrative of the algorithms that may be implemented and can be varied in implementations and embodiments of the principles described herein.

Accordingly, in some embodiments, the techniques described herein may be embodied in computer-executable instructions implemented as software, including as application software, system software, firmware, middleware, embedded code, or any other suitable type of computer code. Such computer-executable instructions may be written using any of a number of suitable programming languages and/or programming or scripting tools, and also may be compiled as executable machine language code or intermediate code that is executed on a framework or virtual machine.

When techniques described herein are embodied as computer-executable instructions, these computer-executable instructions may be implemented in any suitable manner, including as a number of functional facilities, each providing one or more operations to complete execution of algorithms operating according to these techniques. A "functional facility," however instantiated, is a structural component of a computer system that, when integrated with and executed by one or more computers, causes the one or more computers to perform a specific operational role. A functional facility may be a portion of or an entire software element. For example, a functional facility may be implemented as a function of a process, or as a discrete process, or as any other suitable unit of processing. If techniques described herein are implemented as multiple functional facilities, each functional facility may be implemented in its own way; all need not be implemented the same way. Additionally, these functional facilities may be executed in parallel and/or serially, as appropriate, and may pass information between one another using a shared memory on the computer(s) on which they are executing, using a message passing protocol, or in any other suitable way.

Generally, functional facilities include routines, programs, objects, components, data structures, etc. that perform particular tasks or implement particular abstract data types. Typically, the functionality of the functional facilities may be combined or distributed as desired in the systems in which they operate. In some implementations, one or more functional facilities carrying out techniques herein may together form a complete software package. These functional facilities may, in alternative embodiments, be adapted to interact with other, unrelated functional facilities and/or processes, to implement a software program application. In other implementations, the functional facilities may be adapted to interact with other functional facilities in such a way as form an operating system, including the Windows® operating system, available from the Microsoft® Corporation of Redmond, Washington. In other words, in some implementations, the functional facilities may be implemented alternatively as a portion of or outside of an operating system.

Some exemplary functional facilities have been described herein for carrying out one or more tasks. It should be appreciated, though, that the functional facilities and division of tasks described is merely illustrative of the type of functional facilities that may implement the exemplary techniques described herein, and that embodiments are not limited to being implemented in any specific number, division, or type of functional facilities. In some implementations, all functionality may be implemented in a single functional facility. It should also be appreciated that, in some implementations, some of the functional facilities described herein may be implemented together with or separately from others (i.e., as a single unit or separate units), or some of these functional facilities may not be implemented.

Computer-executable instructions implementing the techniques described herein (when implemented as one or more functional facilities or in any other manner) may, in some embodiments, be encoded on one or more computer-readable media to provide functionality to the media. Computer-readable media include magnetic media such as a hard disk drive, optical media such as a Compact Disk (CD) or a Digital Versatile Disk (DVD), a persistent or non-persistent solid-state memory (e.g., Flash memory, Magnetic RAM, etc.), or any other suitable storage media. Such a computer-readable medium may be implemented in any suitable manner, including as computer-readable storage media 1506 of FIG. 15 described above (i.e., as a portion of a computing device 1500) or as a stand-alone, separate storage medium. As used herein, "computer-readable media" (also called "computer-readable storage media") refers to tangible storage media. Tangible storage media are non-transitory and have at least one physical, structural component. In a "computer-readable medium," as used herein, at least one physical, structural component has at least one physical property that may be altered in some way during a process of creating the medium with embedded information, a process of recording information thereon, or any other process of encoding the medium with information. For example, a magnetization state of a portion of a physical structure of a computer-readable medium may be altered during a recording process.

Further, some techniques described above comprise acts of storing information (e.g., data and/or instructions) in certain ways for use by these techniques. In some implementations of these techniques—such as implementations where the techniques are implemented as computer-executable instructions—the information may be encoded on a computer-readable storage media. Where specific structures are described herein as advantageous formats in which to store this information, these structures may be used to impart a physical organization of the information when encoded on the storage medium. These advantageous structures may then provide functionality to the storage medium by affecting operations of one or more processors interacting with the information; for example, by increasing the efficiency of computer operations performed by the processor(s).

In some, but not all, implementations in which the techniques may be embodied as computer-executable instructions, these instructions may be executed on one or more suitable computing device(s) operating in any suitable computer system, including the exemplary computer system of FIG. 15, or one or more computing devices (or one or more processors of one or more computing devices) may be programmed to execute the computer-executable instructions. A computing device or processor may be programmed to execute instructions when the instructions are stored in a manner accessible to the computing device or processor, such as in a data store (e.g., an on-chip cache or instruction register, a computer-readable storage medium accessible via a bus, a computer-readable storage medium accessible via one or more networks and accessible by the device/processor, etc.). Functional facilities comprising these computer-executable instructions may be integrated with and direct the operation of a single multi-purpose programmable digital computing device, a coordinated system of two or more multi-purpose computing devices sharing processing power and jointly carrying out the techniques described herein, a single computing device or coordinated system of computing device (co-located or geographically distributed) dedicated to executing the techniques described herein, one or more Field-Programmable Gate Arrays (FPGAs) for carrying out the techniques described herein, or any other suitable system.

FIG. 15 illustrates one exemplary implementation of a computing device in the form of a computing device 1500 that may be used in a system implementing techniques described herein, although others are possible. It should be appreciated that FIG. 15 is intended neither to be a depiction of necessary components for a computing device to operate as a means for receiving and analyzing signals from a system for determining the malignant potential of a pancreatic cyst in accordance with the principles described herein, nor a comprehensive depiction.

Computing device 1500 may comprise at least one processor 1502, a network adapter 1504, and computer-readable storage media 1506. Computing device 1500 may be, for example, a desktop or laptop personal computer, a personal digital assistant (PDA), a smart mobile phone, a server, a wireless access point or other networking element, or any other suitable computing device. Network adapter 1504 may be any suitable hardware and/or software to enable the computing device 1500 to communicate wired and/or wirelessly with any other suitable computing device over any suitable computing network. The computing network may include wireless access points, switches, routers, gateways, and/or other networking equipment as well as any suitable wired and/or wireless communication medium or media for exchanging data between two or more computers, including the Internet. Computer-readable storage media 1506 may be adapted to store data to be processed and/or instructions to be executed by processor 1502. Processor 1502 enables processing of data and execution of instructions. The data and instructions may be stored on the computer-readable storage media 1506 and may, for example, enable communication between components of the computing device 1500.

The data and instructions stored on computer-readable storage media 1506 may comprise computer-executable instructions implementing techniques which operate according to the principles described herein. In the example of FIG. 15, computer-readable storage media 1506 stores computer-executable instructions implementing various facilities and storing various information as described above. Computer-readable storage media 1506 may store computer-executable instructions for receiving and processing signals from a system for determining the malignant potential of a pancreatic cyst, and displaying results on a screen.

While not illustrated in FIG. 15, a computing device may additionally have one or more components and peripherals, including input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computing device may receive input information through speech recognition or in other audible format.

Described thus far are embodiments of an approach that uses LSS to solve the difficult problem of identifying pre-cancerous and early cancerous lesions in the pancreas, wherein an apparatus for diagnosing pancreatic cysts using LSS may include a needle-based LSS instrument for in vivo use during EUS-FNA procedures.

Various aspects of the described embodiments may be used alone, in combination, or in a variety of arrangements not specifically discussed in the embodiments described in the foregoing, and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

A spatial gating probe may be embodied in different configurations. Example configurations may include any combination or combinations of configurations (1) through (22) as described below.

(1) A spatial gating probe for performing light scattering spectroscopy on tissue is provided, comprising: a housing; and a plurality of fiber-optic cables disposed within the housing, wherein: the plurality of fiber-optic cables comprise at least one source fiber and at least one detector fiber; the at least one source fiber is configured to emit light onto the tissue; and the at least one detector fiber is configured to receive light reflected from the tissue.

(2) The spatial gating probe of configuration (1), wherein the tissue is a pancreatic cyst; the spatial gating probe is configured to be inserted inside the pancreatic cyst; the at least one source fiber is configured to emit light onto an inside surface of the pancreatic cyst; and the at least one detector fiber is configured to receive light reflected from the inside surface of the pancreatic cyst.

(3) The spatial gating probe of configuration (1), wherein the at least one detector fiber comprises at least one first detector fiber and at least one second detector fiber; the at least one first detector fiber is disposed at a distance $d_1$ from the at least one source fiber; the at least one second detector fiber is disposed at a distance $d_2$ from the at least one source fiber; and $d_2$ is greater than $d_1$.

(4) The spatial gating probe of configuration (3), wherein the at least one first detector fiber is configured to receive light reflected from a surface of the pancreatic cyst; and the at least one second detector fiber is configured to receive light reflected from a portion of the pancreatic cyst deeper than the surface of the pancreatic cyst.

(5) The spatial gating probe of configuration (1), wherein the at least one source fiber is connected to a broadband light source.

(6) The spatial gating probe of configuration (1), wherein the spatial gating probe is disposed at the end of a fixed length tube.

(7) The spatial gating probe of configuration (1), wherein the at least one detector fiber is connected to at least one spectrometer.

(8) The spatial gating probe of configuration (1), wherein the plurality of fiber-optic cables are arranged in a hexagonal pattern.

(9) The spatial gating probe of configuration (8), wherein the at least one source fiber is disposed on an outer edge of the hexagonal pattern.

(10) The spatial gating probe of configuration (3), wherein $d_2$ is equal to approximately 240 µm and $d_1$ is equal to approximately 120 µm.

(11) The spatial gating probe of configuration (1), wherein each of the plurality of fiber-optic cables has a diameter of approximately 100 µm, and the housing has a diameter of approximately 450 µm.

(12) The spatial gating probe of configuration (1), wherein the at least one source fiber is configured to emit light in a direction parallel to the housing.

(13) The spatial gating probe of configuration (1), wherein the at least one source fiber is configured to emit light in a direction perpendicular to the housing.

(14) The spatial gating probe of configuration (13), wherein the lens is configured to collimate the light emitted from the at least one source fiber.

(15) The spatial gating probe of configuration (3), wherein the at least one first detector fiber is configured to obtain a first spectrum, and the at least one second detector fiber is configured to obtain a second spectrum.

(16) The spatial gating probe of configuration (15), wherein the first spectrum and second spectrum are analyzed to isolate light reflected from an epithelium layer of the pancreatic cyst in order to determine the malignant potential of the pancreatic cyst.

(17) The spatial gating probe of configuration (16), wherein the second spectrum obtained by the at least one second detector fiber is subtracted from the first spectrum obtained by the at least one first detector fiber in order to isolate light reflected from the epithelium layer.

(18) The spatial gating probe of configuration (3), wherein the at least one first detector fiber comprises three detector fibers, and the at least one second detector fiber comprises three detector fibers.

(19) The spatial gating probe of configuration (1), wherein the spatial gating probe is configured to measure a plurality of locations on the tissue.

(20) The spatial gating probe of configuration (12), wherein the spatial gating probe is configured to move and/or change an angle of orientation in order to measure a plurality of locations on the tissue.

(21) The spatial gating probe of configuration (13), wherein the spatial gating probe is configured to rotate in order to measure a plurality of locations on the tissue.

(22) The spatial gating probe of configuration (15), wherein the first spectrum corresponds to light reflected from the surface of the pancreatic cyst, and the second spectrum corresponds to light reflected from a portion of the pancreatic cyst deeper than the surface.

Apparatus for determining a malignant potential of a pancreatic cyst may be embodied in different configurations. Example configurations may include any combination or combinations of configurations (23) through (46) as described below.

(23) An apparatus for determining a malignant potential of a pancreatic cyst is provided, comprising: a fixed-length tube; an endoscopic ultrasound-guided fine needle aspiration (EUS-FNA) needle disposed at an end of the fixed-length tube; and a spatial gating probe disposed within the EUS-FNA needle, the spatial gating probe comprising: a housing; and a plurality of fiber-optic cables disposed within the housing, wherein: the plurality of fiber-optic cables comprise at least one source fiber and at least one detector fiber; the at least one source fiber is configured to emit light onto the pancreatic cyst; and the at least one detector fiber is configured to receive light reflected from the pancreatic cyst.

(24) The apparatus of (23), wherein the fixed-length tube is configured to be inserted orally into the patient; the EUS-FNA needle is configured to be inserted inside the pancreatic cyst; the at least one source fiber is configured to emit light onto an inside surface of the pancreatic cyst; and the at least one detector fiber is configured to receive light reflected from the inside surface of the pancreatic cyst.

(25) The apparatus of (23), wherein the at least one detector fiber comprises at least one first detector fiber and at least one second detector fiber; the at least one first detector fiber is disposed at a distance $d_1$ from the at least one source fiber; the at least one second detector fiber is disposed at a distance $d_2$ from the at least one source fiber; and $d_2$ is greater than $d_1$.

(26) The apparatus of (25), wherein the at least one first detector fiber is configured to receive light reflected from a surface of the pancreatic cyst; and the at least one second detector fiber is configured to receive light reflected from a portion of the pancreatic cyst deeper than the surface of the pancreatic cyst.

(27) The apparatus of (23), wherein the apparatus further comprises a broadband light source, and wherein the at least one source fiber is connected, through the tube, to the broadband light source.

(28) The apparatus of (23), wherein the spatial gating probe is configured to extend beyond a tip of the EUS-FNA needle.

(29) The apparatus of (23), wherein the apparatus further comprises at least one spectrometer, wherein the at least one detector fiber is connected to the at least one spectrometer.

(30) The apparatus of (23), wherein the plurality of fiber-optic cables are arranged in a hexagonal pattern.

(31) The apparatus of (30), wherein the at least one source fiber is disposed on an outer edge of the hexagonal pattern.

(32) The apparatus of (25), wherein $d_2$ is equal to approximately 240 μm and $d_1$ is equal to approximately 120 μm.

(33) The apparatus of (23), wherein each of the plurality of fiber-optic cables has a diameter of approximately 100 μm, and the housing of the spatial gating probe has a diameter of approximately 450 μm.

(34) The apparatus of (23), wherein the at least one source fiber is configured to emit light in a direction parallel to the EUS-FNA needle.

(35) The apparatus of (23), wherein the at least one source fiber is configured to emit light in a direction perpendicular to the EUS-FNA needle.

(36) The apparatus of (35), wherein the spatial gating probe further comprises a lens, and wherein the lens is configured to collimate the light emitted from the at least one source fiber.

(37) The apparatus of (25), wherein the apparatus further comprises at least one first spectrometer and at least one second spectrometer, and wherein: the at least one first detector fiber is connected to the at least one first spectrometer; the at least one second detector fiber is connected to the at least one second spectrometer; and the at least one first detector fiber is configured to obtain a first spectrum, and the at least one second detector fiber is configured to obtain a second spectrum.

(38) The apparatus of (37), wherein the at least one first and second spectrometers are configured to analyze the first and second spectrum to isolate light reflected from an epithelium layer of the pancreatic cyst in order to determine the malignant potential of the pancreatic cyst.

(39) The apparatus of (38), wherein the at least one first and second spectrometers are configured to analyze the first and second spectrum to isolate light from the epithelium layer of the pancreatic cyst at least by subtracting the second spectrum from the first spectrum.

(40) The apparatus of (25), wherein the at least one first detector fiber comprises three detector fibers, and the at least one second detector fiber comprises three detector fibers.

(41) The apparatus of (23), wherein the spatial gating probe is configured to measure a plurality of locations on the pancreatic cyst.

(42) The apparatus of (34), wherein the spatial gating probe is configured to move and/or change an angle of orientation in order to measure a plurality of locations on the pancreatic cyst.

(43) The apparatus of (35), wherein the spatial gating probe is configured to rotate in order to measure a plurality of locations on the pancreatic cyst.

(44) The apparatus of (37), wherein the first spectrum corresponds to light reflected from the surface of the pancreatic cyst, and the second spectrum corresponds to light reflected from a portion of the pancreatic cyst deeper than the surface.

(45) The apparatus of (28), wherein the apparatus further comprises a probe latching mechanism configured to lock a position of the spatial gating probe.

(46) The apparatus of (45), wherein the probe latching mechanism comprises a button. Methods for determining a malignant potential of a pancreatic cyst of a patient may include various processes. Example methods may include any combination or combinations of processes (47) through (68) as described below.

(47) A method for determining a malignant potential of a pancreatic cyst of a patient, comprising: inserting a spatial gating probe into the pancreatic cyst, the spatial gating probe comprising: a housing; and a plurality of fiber-optic cables disposed within the housing, wherein the plurality of fiber-optic fibers comprise at least one source fiber and at least one detector fiber; emitting light, from the at least source fiber, onto an inside surface of the pancreatic cyst; receiving, via the at least one detector fiber, light reflected from the inside surface of the pancreatic cyst; and determining, at least from the light received via the at least one detector fiber, the malignant potential of the pancreatic cyst.

(48) The method of (47), further comprising orally inserting a fixed-length tube into the patient, wherein the spatial gating probe is disposed at the end of the fixed-length tube.

(49) The method of (47), wherein the at least one detector fiber comprises at least one first detector fiber and at least one second detector fiber, and wherein receiving, via the at least one detector fiber, light reflected from the inside surface of the pancreatic cyst comprises: obtaining, via the at least one first detector fiber, a first spectrum; and obtaining, via the at least one second detector fiber, a second spectrum.

(50) The method of (49), further comprising analyzing the first and second spectrum to isolate light reflected from an epithelium layer of the pancreatic cyst in order to determine the malignant potential of the pancreatic cyst.

(51) The method of (50), wherein analyzing the first and second spectrum to isolate light reflected from the epithelium layer of the pancreatic cyst comprises subtracting the second spectrum from the first spectrum.

(52) The method of (49), wherein the first spectrum corresponds to light reflected from the surface of the pancreatic cyst, and the second spectrum corresponds to light reflected from a portion of the pancreatic cyst deeper than the surface.

(53) The method of (49), wherein the at least one first detector fiber is disposed at a distance $d_1$ from the at least one source fiber; the at least one second detector fiber is disposed at a distance $d_2$ from the at least one source fiber; and $d_2$ is greater than $d_1$.

(54) The method of (47), wherein the at least one source fiber is connected to a broadband light source.

(55) The method of (47), wherein the plurality of fiber-optic cables are arranged in a hexagonal pattern.

(56) The method of (55), wherein the at least one source fiber is disposed on an outer edge of the hexagonal pattern.

(57) The method of (53), wherein $d_2$ is equal to approximately 240 µm and $d_1$ is equal to approximately 120 µm.

(58) The method of (47), wherein each of the plurality of fiber-optic cables has a diameter of approximately 100 µm, and the housing has a diameter of approximately 450 µm.

(59) The method of (47), wherein emitting light, from the at least source fiber, onto an inside surface of the pancreatic cyst comprises emitting light onto a plurality of locations of the inside surface of the pancreatic cyst; and receiving, via the at least one detector fiber, light reflected from the inside surface of the pancreatic cyst comprises receiving light reflected from the plurality of locations of the inside surface of the pancreatic cyst.

(60) The method of (59), wherein the spatial gating probe is configured to emit light in a direction parallel to the housing.

(61) The method of (59), wherein the spatial gating probe is configured to emit light in a direction perpendicular to the housing.

(62) The method of (60), wherein the spatial gating probe is configured to move in order to emit light onto and receive light reflected from the plurality of locations of the inside surface of the pancreatic cyst.

(63) The method of (61), wherein the spatial gating probe is configured to rotate in order to emit light onto and receive light reflected from the plurality of locations of the inside surface of the pancreatic cyst.

(64) The method of (47), further comprising extracting fluid from the pancreatic cyst, and wherein the malignant potential of the pancreatic cyst is further determined by analyzing the fluid extracted from the pancreatic cyst.

(65) The method of (64), wherein analyzing the fluid extracted from the pancreatic cyst comprises performing a cytology on the fluid.

(66) The method of (47), wherein determining, at least from the light received via the at least one detector fiber, the malignant potential of the pancreatic cyst comprises determining a diagnostic parameter $\Delta$.

(67) The method of (66), wherein the diagnostic parameter $\Delta$ correspond to enlarged nuclei in measured cells of the pancreatic cyst.

(68) The method of (66), wherein determining, at least from the light received via the at least one detector fiber, the malignant potential of the pancreatic cyst further comprises: classifying the pancreatic cyst as benign if the diagnostic parameter $\Delta$ is less than 0.1; classifying the pancreatic cyst as low-grade dysplasia if the diagnostic parameter $\Delta$ is greater than or equal to 0.1 and less than 0.2; and classifying the pancreatic cyst as high-grade dysplasia if the diagnostic parameter $\Delta$ is greater than or equal to 0.2.

At least one non-transitory computer-readable storage medium having stored thereon instructions that, when executed by at least one processor, may perform a method for determining a malignant potential of a pancreatic cyst of a patient, and the method may include various processes. Example configurations may include any combination or combinations of configurations (69) through (76) as described below.

(69) At least one non-transitory computer-readable storage medium having stored thereon instructions that, when executed by at least one processor, perform a method, the method comprising: obtaining at least one spectrum, from a spatial gating probe, corresponding to light reflected from an inside surface of a pancreatic cyst; determining, at least from the at least one spectrum, a malignant potential of the pancreatic cyst.

(70) The at least one non-transitory computer-readable storage medium of (69), wherein obtaining the at least one spectrum comprises: receiving a first spectrum from at least one first fiber-optic cable of the spatial gating probe; and receiving a second spectrum from at least one second fiber-optic cable of the spatial gating probe.

(71) The at least one non-transitory computer-readable storage medium of (70), wherein the first spectrum corresponds to light reflected from the surface of the pancreatic cyst, and the second spectrum corresponds to light reflected from a port of the pancreatic cyst deeper than the surface.

(72) The at least one non-transitory computer-readable storage medium of (70), wherein the method further comprises: analyzing the first and second spectrum to isolate light reflected from an epithelium layer of the pancreatic cyst in order to determine the malignant potential of the pancreatic cyst.

(73) The at least one non-transitory computer-readable storage medium of (72), wherein analyzing the first and second spectrum to isolate light reflected from the epithelium layer of the pancreatic cyst comprises subtracting the second spectrum from the first spectrum.

(74) The at least one non-transitory computer-readable storage medium of (69), wherein determining, at least from the at least one spectrum, the malignant potential of the pancreatic cyst comprises determining a diagnostic parameter $\Delta$.

(75) The at least one non-transitory computer-readable storage medium of (74), wherein the diagnostic parameter $\Delta$ corresponds to enlarged nuclei in measured cells of the pancreatic cyst.

(76) The at least one non-transitory computer-readable storage medium of (74), wherein determining, at least from the at least one spectrum, the malignant potential of the pancreatic cyst further comprises: classifying the pancreatic cyst as benign if the diagnostic parameter $\Delta$ is less than 0.1; classifying the pancreatic cyst as low-grade dysplasia if the diagnostic parameter $\Delta$ is greater than or equal to 0.1 and less than 0.2; and classifying the pancreatic cyst as high-grade dysplasia if the diagnostic parameter $\Delta$ is greater than or equal to 0.2.

What is claimed is:

1. A spatial gating probe for performing light scattering spectroscopy on tissue, the spatial gating probe comprising:
    a housing;
    a plurality of fiber-optic cables disposed within the housing, wherein:
        the plurality of fiber-optic cables comprises at least one source fiber and at least one detector fiber;
        the at least one source fiber is configured to emit light onto the tissue;
        the at least one detector fiber is configured to receive light reflected from the tissue;

the plurality of fiber-optic cables being constructed and arranged in a hexagonal shape such that the at least one source fiber is disposed at an outer edge of the hexagonal shape;
the at least one detector fiber comprises at least one first detector fiber and at least one second detector fiber;
the at least one first detector fiber is disposed at a distance $d_1$ from the at least one source fiber;
the at least one second detector fiber is disposed at a distance $d_2$ from the at least one source fiber; and
$d_2$ is greater than $d_1$; and
first and second spectrometers,
wherein the at least one first detector fiber is configured to obtain a first spectrum, and the at least one second detector fiber is configured to obtain a second spectrum,
wherein the first and second spectrometers are configured to analyze, respectively, the first spectrum and the second spectrum to subtract the second spectrum obtained by the at least one second detector fiber from the first spectrum obtained by the at least one first detector fiber,
wherein the first spectrum and second spectrum are unpolarized signals.

2. The spatial gating probe of claim 1, wherein:
the spatial gating probe is configured to be inserted inside a pancreatic cyst;
the at least one source fiber is configured to emit light onto an inside surface of the pancreatic cyst; and
the at least one detector fiber is configured to receive light reflected from the inside surface of the pancreatic cyst.

3. The spatial gating probe of claim 1, wherein:
the at least one first detector fiber is configured to receive light reflected from a surface of a pancreatic cyst; and
the at least one second detector fiber is configured to receive light reflected from a portion of the pancreatic cyst deeper than the surface of the pancreatic cyst.

4. The spatial gating probe of claim 1, wherein $d_2$ is equal to 240 μm and $d_1$ is equal to 120 μm.

5. The spatial gating probe of claim 1, wherein the first and second spectrometers are configured to analyze respectively the first spectrum and second spectrum to isolate light reflected from an epithelium layer of a pancreatic cyst in order to determine a malignant potential of the pancreatic cyst.

6. The spatial gating probe of claim 1, wherein the first spectrum corresponds to light reflected from a surface of a pancreatic cyst, and the second spectrum corresponds to light reflected from a portion of the pancreatic cyst deeper than the surface.

7. An apparatus for determining a malignant potential of a pancreatic cyst, the apparatus comprising:
a fixed-length tube;
an endoscopic ultrasound-guided fine needle aspiration (EUS-FNA) needle disposed at an end of the fixed-length tube; and
a spatial gating probe disposed within the EUS-FNA needle, the spatial gating probe comprising:
a housing; and
a plurality of fiber-optic cables disposed within the housing, wherein:
the plurality of fiber-optic cables comprises at least one source fiber and at least one detector fiber;
the at least one source fiber is configured to emit light onto the pancreatic cyst;
the at least one detector fiber is configured to receive light reflected from the pancreatic cyst;
the plurality of fiber-optic cables being constructed and arranged in a hexagonal shape such that the at least one source fiber is disposed at an outer edge of the hexagonal shape housing;
the at least one detector fiber comprises at least one first detector fiber and at least one second detector fiber;
the at least one first detector fiber is disposed at a distance $d_1$ from the at least one source fiber;
the at least one second detector fiber is disposed at a distance $d_2$ from the at least one source fiber; and
$d_2$ is greater than $d_1$
first and second spectrometers,
wherein the at least one first detector fiber is configured to obtain a first spectrum, and the at least one second detector fiber is configured to obtain a second spectrum,
wherein the first and second spectrometers are configured to analyze, respectively, the first spectrum and the second spectrum to subtract the second spectrum obtained by the at least one second detector fiber from the first spectrum obtained by the at least one first detector fiber,
wherein the first spectrum and second spectrum are unpolarized signals.

8. The apparatus of claim 7, wherein:
the fixed-length tube is configured to be inserted orally into a patient;
the EUS-FNA needle is configured to be inserted inside the pancreatic cyst;
the at least one source fiber is configured to emit light onto an inside surface of the pancreatic cyst; and
the at least one detector fiber is configured to receive light reflected from the inside surface of the pancreatic cyst.

9. The apparatus of claim 7, wherein:
the at least one first detector fiber is configured to receive light reflected from a surface of the pancreatic cyst; and
the at least one second detector fiber is configured to receive light reflected from a portion of the pancreatic cyst deeper than the surface of the pancreatic cyst.

10. The apparatus of claim 7, wherein $d_2$ is equal to 240 μm and $d_1$ is equal to 120 μm.

11. The apparatus of claim 7, wherein:
the at least one first detector fiber is connected to the at least one first spectrometer; and
the at least one second detector fiber is connected to the at least one second spectrometer.

12. The apparatus of claim 11, wherein the at least one first and second spectrometers are configured to analyze the first and second spectrum to isolate light reflected from an epithelium layer of the pancreatic cyst in order to determine the malignant potential of the pancreatic cyst.

13. The apparatus of claim 11, wherein the first spectrum corresponds to light reflected from the surface of the pancreatic cyst, and the second spectrum corresponds to light reflected from a portion of the pancreatic cyst deeper than the surface.

14. The spatial gating probe of claim 1, wherein the housing is configured to contact the tissue.

15. The apparatus of claim 7, wherein the housing is configured to contact the pancreatic cyst.

16. The apparatus of claim 7, wherein the EUS-FNA needle is either a 22 gauge or a 19 gauge.

17. The apparatus of claim 7, wherein an internal diameter of the EUS-FNA needle is less than or equal to 0.91 mm.

* * * * *